United States Patent
Emslander et al.

(10) Patent No.: US 11,510,804 B2
(45) Date of Patent: Nov. 29, 2022

(54) MUSCLE OR JOINT SUPPORT ARTICLE WITH A STRAP

(71) Applicant: 3M INNOVATIVE PROPERTIES COMPANY, St. Paul, MN (US)

(72) Inventors: Diane L. Emslander, Grant, MN (US); Dominic J. Julian, Woodbury, MN (US); Nathan A. Abel, Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 732 days.

(21) Appl. No.: 16/465,793

(22) PCT Filed: Nov. 30, 2017

(86) PCT No.: PCT/US2017/063895
§ 371 (c)(1),
(2) Date: May 31, 2019

(87) PCT Pub. No.: WO2018/102521
PCT Pub. Date: Jun. 7, 2018

(65) Prior Publication Data
US 2019/0388263 A1     Dec. 26, 2019

Related U.S. Application Data

(60) Provisional application No. 62/579,301, filed on Oct. 31, 2017, provisional application No. 62/429,381, filed on Dec. 2, 2016.

(51) Int. Cl.
*A61F 5/32*     (2006.01)
*A61F 5/01*     (2006.01)
(Continued)

(52) U.S. Cl.
CPC .............. *A61F 5/32* (2013.01); *A61F 5/0106* (2013.01); *A61F 5/019* (2013.01); *A61F 5/0111* (2013.01);
(Continued)

(58) Field of Classification Search
CPC ........ A61F 5/32; A61F 5/0106; A61F 5/0111; A61F 5/0118; A61F 5/019; A61F 5/02;
(Continued)

(56) References Cited

U.S. PATENT DOCUMENTS 3,825,379 A    6/1974   Lohkamp
3,849,241 A    11/1974  Butin
(Continued)

FOREIGN PATENT DOCUMENTS

CA     2775687          10/2013
CA     2775687 A1 *     10/2013   ........... A61F 13/023
(Continued)

OTHER PUBLICATIONS

Wente, "Superfine Thermoplastic Fibers",Industrial Engineering Chemistry, 1956, vol. 48, No. 8, pp. 1342-1346.
(Continued)

*Primary Examiner* — Tarla R Patel
(74) *Attorney, Agent, or Firm* — Philip P. Soo; Sandra K. Nowak

(57) ABSTRACT

The present application generally relates to support articles and methods of making and using them. The support articles of the present disclosure provide compression and/or stabilization of sore joints of muscles. In some embodiments, the compression and/or enhanced stabilization is provided, at least in part, by one or more straps. In some embodiments, the support articles also include one or more reinforcing portions. In some embodiments, the support articles can easily be applied by a non-trained user and can be worn in
(Continued)

many conditions (including, for example, in the shower or during exercise) for up to three days. The support articles have a relatively slim profile and are thus discreet such that they can be worn under clothing without being noticeable.

18 Claims, 15 Drawing Sheets

(51) Int. Cl.
    *A61F 5/02*     (2006.01)
    *A61F 5/03*     (2006.01)
    *A61F 5/055*     (2006.01)
    *A61F 5/10*     (2006.01)
    *A61L 15/12*     (2006.01)

(52) U.S. Cl.
    CPC .............. *A61F 5/0118* (2013.01); *A61F 5/02* (2013.01); *A61F 5/03* (2013.01); *A61F 5/055* (2013.01); *A61F 5/10* (2013.01); *A61L 15/125* (2013.01)

(58) Field of Classification Search
    CPC .... A61F 5/03; A61F 5/055; A61F 5/10; A61F 5/30; A61F 5/01; A61L 15/125
    See application file for complete search history.

(56) References Cited

U.S. PATENT DOCUMENTS

| | | |
|---|---|---|
| 5,116,675 A | 5/1992 | Nash-Morgan |
| 5,176,952 A | 1/1993 | Joseph |
| 5,232,770 A | 8/1993 | Joseph |
| 5,238,733 A | 8/1993 | Joseph |
| 5,248,455 A | 9/1993 | Joseph |
| 5,258,220 A | 11/1993 | Joseph |
| 5,336,552 A | 8/1994 | Strack |
| 5,382,400 A | 1/1995 | Pike |
| 5,496,605 A * | 3/1996 | Augst .................. C09J 7/21 428/354 |
| 5,498,463 A | 3/1996 | McDowall |
| 5,512,358 A | 4/1996 | Shawver |
| 5,545,464 A | 8/1996 | Stokes |
| 5,695,868 A | 12/1997 | McCormack |
| 6,098,616 A * | 8/2000 | Lundy, Jr. .............. A61F 5/08 128/206.25 |
| 6,107,219 A * | 8/2000 | Joseph .................. A61L 15/42 442/364 |
| 6,238,411 B1 * | 5/2001 | Thorner ............. A61M 29/00 606/199 |
| 6,703,120 B1 | 3/2004 | Ko |
| 6,730,397 B2 | 5/2004 | Melancon |
| 7,393,334 B2 | 7/2008 | Tornai |
| 7,407,709 B2 | 8/2008 | Zhou |
| 7,793,661 B2 * | 9/2010 | Macken ................. A61F 5/56 602/41 |
| 7,807,268 B2 | 10/2010 | Zhou |
| 8,541,481 B2 | 9/2013 | Determan |
| 8,758,285 B2 * | 6/2014 | Dallison ................ A61F 13/12 602/61 |
| 8,814,818 B2 | 8/2014 | Bushby |
| 8,822,559 B2 | 9/2014 | Zoller |
| 8,822,560 B2 | 9/2014 | Seth |
| 9,017,771 B2 | 4/2015 | Determan |
| 9,359,529 B2 | 6/2016 | Liu |
| 2003/0069530 A1 | 4/2003 | Satou |
| 2003/0149389 A1 | 8/2003 | Daneshvar |
| 2010/0016771 A1 | 1/2010 | Arbesman |
| 2010/0155998 A1 | 6/2010 | Rule |
| 2011/0206924 A1 | 8/2011 | Liu |
| 2012/0175298 A1 * | 7/2012 | Gupta ................. B01D 39/163 210/496 |
| 2013/0040073 A1 | 2/2013 | Pett |
| 2014/0107552 A1 | 4/2014 | Bushby |
| 2014/0220843 A1 | 8/2014 | Liu |
| 2015/0165087 A1 | 6/2015 | Fung |
| 2015/0259495 A1 | 9/2015 | Liu |
| 2015/0299542 A1 | 10/2015 | Determan |
| 2015/0376345 A1 | 12/2015 | Liu |
| 2016/0101208 A1 * | 4/2016 | Topolkaraev ........ D04H 1/4291 604/370 |
| 2017/0081573 A1 | 3/2017 | Kipke |
| 2019/0314187 A1 | 10/2019 | Emslander |
| 2019/0328580 A1 | 10/2019 | Emslander |
| 2021/0137729 A1 | 5/2021 | Ebel |

FOREIGN PATENT DOCUMENTS

| | | | |
|---|---|---|---|
| FR | 2 697 156 | 10/1992 | |
| JP | 2012-223236 | 11/2012 | |
| KR | 0178583 B1 * | 1/1999 | |
| WO | WO-2009050493 A1 * | 4/2009 | .......... A61F 13/023 |
| WO | WO-2010039771 A * | 4/2010 | .............. A61F 5/08 |
| WO | WO 2016-028941 | 2/2016 | |
| WO | WO 2018-102249 | 6/2018 | |
| WO | WO 2018/102272 | 6/2018 | |
| WO | WO 2018/102322 | 6/2018 | |
| WO | WO-2021258220 A1 * | 12/2021 | |

OTHER PUBLICATIONS

Wente, "Manufacture of Superfine Organic Fibers", Report No. 4364 of the Navel Research Laboratories, May 25, 1954, 19pages.
International Search report for PCT International Application No. PCT/US2017/063895 dated Mar. 19, 2018, 4 pages.
Extended European Search Report for EP Patent Application No. 17 87 5420.6, dated Oct. 20, 2020.

* cited by examiner

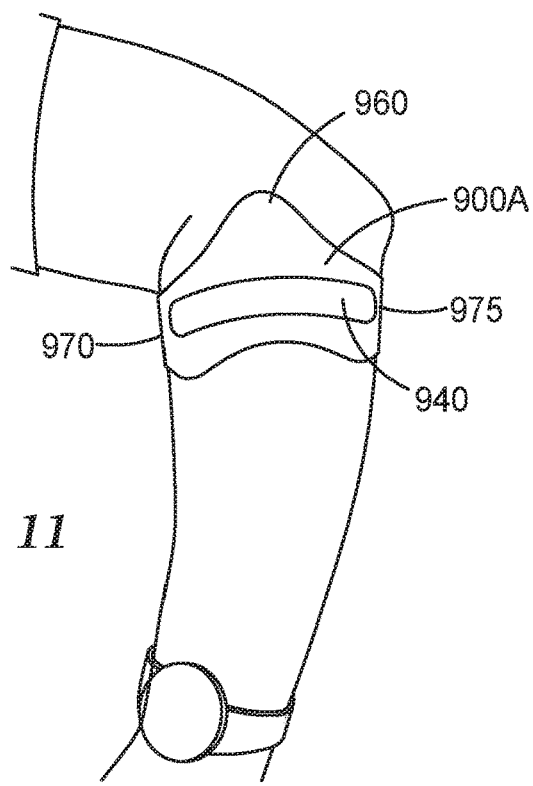
FIG. 11
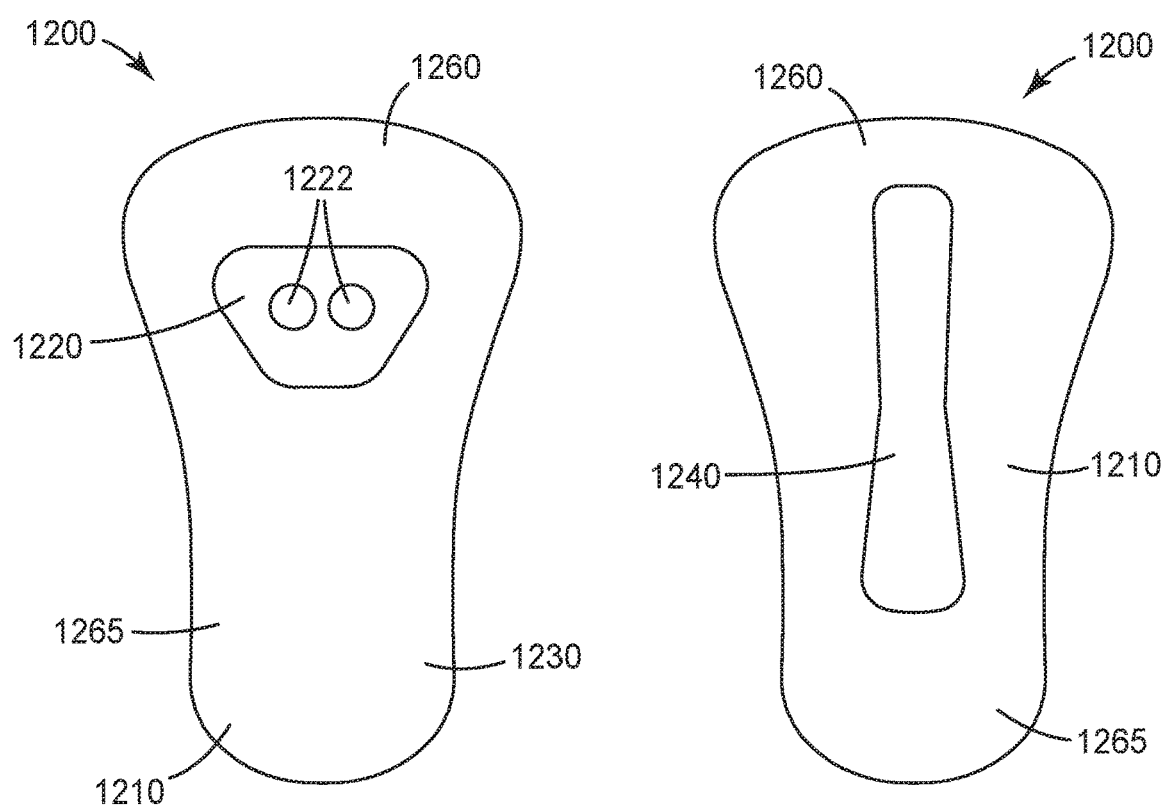
FIG. 12A
FIG. 12B

MUSCLE OR JOINT SUPPORT ARTICLE WITH A STRAP

CROSS REFERENCE TO RELATED APPLICATIONS

This application is a national stage filing under 35 U.S.C. 371 of PCT/US2017/063895, filed Nov. 30, 2017, which claims the benefit of provisional Application No. 62/579301, filed Oct. 31, 2017 and provisional Application No. 62/429381, filed Dec. 2, 2016, the disclosure of which is incorporated by reference in its/their entirety herein.

TECHNICAL FIELD

The present application generally relates to support articles and methods of making and using them.

BACKGROUND

A strained or injured muscle or joint not only causes pain and discomfort, but can make someone feel slower or weaker than normal, all of which can interfere with daily living activities. As such, maintaining healthy skeletal muscles is essential to keeping people moving at their best. Historically, those with injuries or discomfort were instructed to limit or eliminate movement of the injured muscle, tendon, or joint. Today we know that, generally, keeping muscles moving improves circulation, can reduce pain, and/or speeds healing. Over the past twenty years, many innovative devices and techniques have come out of kinesiology science (the science behind muscular and skeletal movement) to help protect and treat injured or sore muscles, tendons, and joints.

Compression wraps, sleeves, and braces offer stabilization of the muscles and joints covered by the wraps, sleeves, and braces. Additionally or alternatively, compression wraps, sleeves, and braces help to reduce pain, swelling, and cramping by increasing circulation and/or reducing fatigue. More specifically, an injured muscle often swells as a result of a build-up of fluid. The fluid build-up can prevent blood from circulating to the injured area, which results in slowing the healing process. Compression therapy generally uses a snug-fitting device to put pressure on the impacted area. The pressure reduces swelling and/or increases circulation by forcing fluid in the impacted area to move back into the blood vessels. As a result, the swelling decreases. Once the swelling has decreased, blood flow may return to the area and promote healing.

Kinesiology tapes (KT tapes) gently lift the skin and tissue attached to an injured muscle so that blood and other body fluids can move more freely in and around that muscle. Additionally, KT tapes can create neuromuscular feedback (called proprioception) that inhibits (relaxes) or facilitates stronger firing of muscles and tendons. This neuromuscular feedback can provide some support to the muscles, tendons, and joints without the bulk and restriction commonly associated with wraps and heavy bracing.

SUMMARY

The inventors of the present disclosure recognized that existing commercial compression and kinesiology tape offerings have some disadvantages. For example, braces and compression sleeves, while highly effective, are bulky and can be challenging to wear discreetly under clothing. Further, braces and compression sleeves can be a significant monetary investment, and/or can get dirty and sweaty during prolonged use. Compression tapes and/or wraps can be challenging for non-professionally trained users to correctly apply at the correct tightness, potentially limiting their effectiveness and/or causing pain or harm. Kinesiology tapes provide good neuromuscular feedback but do not provide significant compression. Some kinesiology tapes do not provide significant support but instead rely on proprioception and/or lift. Further, their ability to provide stabilization is somewhat limited.

The inventors of the present disclosure sought to create disposable and/or relatively inexpensive support articles that offer the best features of braces, compression sleeves, compression wraps, and kinesiology tapes while eliminating or minimizing their drawbacks. The inventors of the present disclosure sought to create support articles that offer muscle or joint stabilization similar to a brace, muscle or joint compression similar to a compression wrap, and/or the slim, discreet profile and neuromuscular feedback of kinesiology tapes.

In some embodiments, the support articles of the present disclosure provide compression, support, and/or stabilization of sore joints, tendons, or muscles. In some embodiments, the compression and/or enhanced stabilization is provided, at least in part, by a strap that extends across a portion of the front (or top) major surface of the support article and, when applied by the user, increases the compression force of the support article on the affected area of the user. As used herein, the term "affected area" relates to the area of the user proximate or adjacent to the joint, tendon, or muscle experiencing soreness, swelling, pain, tenderness, etc. In some embodiments, the support article is patch, cover, sheet, or strip. In some embodiments, the support articles of the present disclosure are noncircumferential (in other words, it does not extend around the circumference of a body part such as, for example, an ankle, leg, arm, etc. in the way that a wrap or elastic bandage (e.g., Ace™ bandage) would extend around the circumference of the body part).

In some embodiments, the support articles of the present disclosure also include one or more reinforcing portions that further enhance the compression, stabilization, and/or support. In some embodiments, the support articles can easily be applied by a non-trained user and can be worn in many conditions (including, for example, in the shower or during exercise) for up to three days. The support articles may also have a relatively slim profile and can thus be discreet such that they can be worn under clothing without being noticeable. Some support articles of the present disclosure are disposable after use. Such disposable support articles cost significantly less than a brace or compression sleeve. In some embodiments, the support articles of the present disclosure eliminate or reduce joint or muscle pain or soreness. In some embodiments, the support articles of the present disclosure have a shape and size tailored for a specific body area. In some embodiments, the support articles of the present disclosure are easy to apply and remove easily and/or without pain.

Some embodiments of the present disclosure relate to a support article including a backing having a front major surface and a rear major surface; an adhesive adjacent to least a portion of the rear major surface of the backing, the adhesive capable of adhering the support article to a user; and a strap attached or adhered to the front major surface of the backing, the strap being capable of stretching across at least a portion of the support article.

Some embodiments of the present disclosure relate to a method of applying a support article, comprising: removing a liner from a rear major surface of the support article to expose an adhesive; positioning the support article adjacent to a user's body in a desired location; applying the support article to the user such that the adhesive contacts the user's skin; putting pressure on the support article to cause the adhesive to adhere to the user's skin; removing one or more liners from a rear major surface of a strap on the support article; grasping one or more portions of the strap and elongating it; and applying the strap to the user such that the strap adhered to the support article or user's skin.

Any of the embodiments described herein can include a release liner adjacent to at least a portion of the adhesive. Any of the embodiments described herein can include a backing including at least one of a polyurethane film, a polyethylene film, a polypropylene film, a PVC film, a nonwoven material, and/or a woven material. Any of the embodiments described herein can include a backing including at least one of a polyolefin, polyester, polyalkylene, polyamide, polystyrene, polyarylsulfone, polydiene, and/or polyurethane. Any of the embodiments described herein can include a backing including conjugate multicomponent melt spun fibers. Any of the embodiments described herein can include a backing having a weight of between about 25 gsm to about 300 gsm. Any of the embodiments described herein can include the backing having a thickness of about 0.01 cm to about 1 cm.

Any of the embodiments described herein can include at least one of the backing or the backing and adhesive combination having a breathability and/or porosity of between about 3 and about 12 mm H$_2$O measured using the pressure drop test. Any of the embodiments described herein can include at least one of the backing or the backing and adhesive combination having a cross-directional tensile strength of between about 4 lbf (17.8 N) and about 9 lbf (40.0 N) and/or a machine-directional tensile strength of between about 5 lbf (22.2 N) and about 10 lbf (44.5 N). Any of the embodiments described herein can include at least one of the backing or the backing and adhesive combination having a cross-directional elongation at break of between about 600% and about 900% and/or a machine-directional elongation at break of between about 350% and about 1000%. Any of the embodiments described herein can include the backing and adhesive forming a conjugate multicomponent system. Any of the embodiments described herein can include the reinforcing portion(s) covering between about 10% and about 75% of the total surface area of the backing.

Any of the embodiments described herein can include the adhesive being a pressure sensitive adhesive and being selected from at least one of the following adhesive classes: polyacrylate adhesives, polyalphaolefin adhesives, polyvinyl acrylates, rubber resin adhesives, silicone adhesives, polydiorganosiloxane polyurea copolymers, and mixtures thereof.

Any of the embodiments described herein can include one or more reinforcing portions. Any of the embodiments described herein can include the adhesive adhering the one or more reinforcing portions to the front or rear major surface of the backing. Any of the embodiments described herein can include the one or more reinforcing portions including at least one of foam or a shaped memory material. Any of the embodiments described herein can include the one or more reinforcing portions comprising: an adhesive layer having first and second major surfaces; a first foam layer adjacent to first major surface of the adhesive layer; a second foam layer adjacent to second major surface of the adhesive layer; a first skin layer adjacent to first foam layer; and a second skin layer adjacent to second foam layer. Any of the embodiments described herein can include microspheres in at least one of the first or second foam layers. Any of the embodiments described herein can include the one or more reinforcing portions having a Shore A hardness is between about 10 and about 100 when measured according to ASTM D2240 and/or a Shore D hardness of between about 10 and about 60 when measured according to ASTM D2240. Any of the embodiments described herein can include the one or more reinforcing portions having a cross-directional tensile strength of between about 13 lbf (57.8 N) and about 28 lbf (129.0 N) and/or a machine-directional tensile strength of between about 16 lbf (71.2 N) and about 31 lbf (137.9 N). Any of the embodiments described herein can include the one or more reinforcing portions having a thickness of between about 2 cm (787 mil) and about 0.051 cm (20 mil). Any of the embodiments described herein can include the one or more reinforcing portions having an elongation at break of between about 10% and about 50%. Any of the embodiments described herein can include at least two reinforcing layers that are on layered on one another. Any of the embodiments described herein can include at least one of the reinforcing portions being separate from the support article and being independently applied by the user before the full support article is applied.

Any of the embodiments described herein can include the support article having a weight of between about 20 gsm and about 500 gsm. Any of the embodiments described herein can include a support article applied to or sized for application to at least one of the IT band, hip, calf, shin, quads, hamstrings, groin, hip flexor, gluteus, outer knee, inner knee, Osgood shlatter, back of knee, front of knee, Achilles tendon, ankle, ball of foot, top of foot, heel, toe, finger, SI joint, low back, middle back, ribs, spine, abdominal, neck, shoulder, rotator cuff, AC joint, wrist, elbow, thumb, bicep, and/or tricep.

BRIEF DESCRIPTION OF DRAWINGS

FIG. 11 is a schematic drawing of the support article of any of FIGS. 9-10D in use.

FIGS. 12A and 12B are respective front and rear views of another exemplary embodiment of a support article in accordance with the teachings of the present disclosure.

Figure 1A:
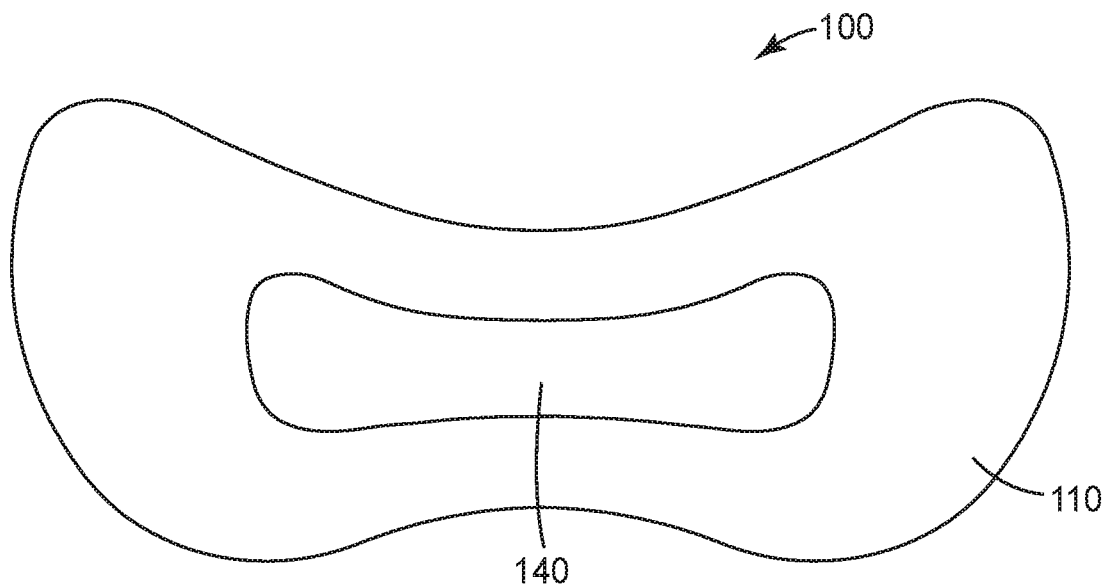
FIGS. 1A and 1B are respective front and rear views of one exemplary embodiment of a support article in accordance with the teachings of the present disclosure.
Figure 1B:
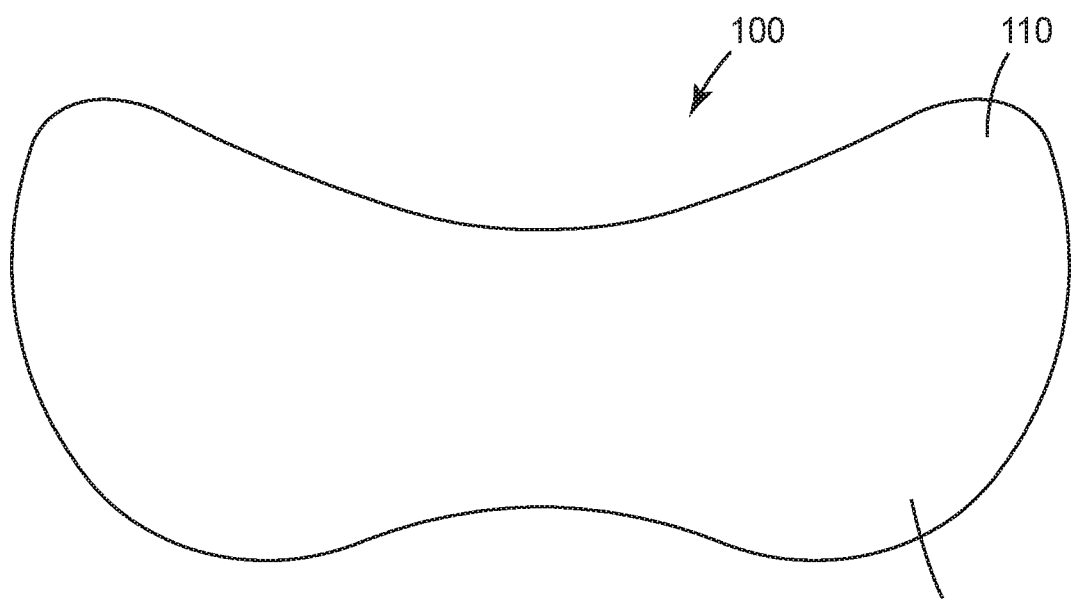

In the following detailed description, reference may be made to the above-described set of drawings in which are shown by way of illustration several exemplary embodiments. It is to be understood that other embodiments are contemplated and may be made without departing from the scope or spirit of the present disclosure.

DETAILED DESCRIPTION

Various embodiments and implementations will be described in detail. These embodiments should not be construed as limiting the scope of the present application in any manner, and changes and modifications may be made without departing from the spirit and scope of the inventions described herein. Further, only some end uses have been discussed herein, but end uses not specifically described herein are included within the scope of the present application. For example, the support article can be a patch. A patch is merely one exemplary embodiment. As used herein, the term "patch" refers to a piece of material used to cover an injured or sensitive area of the body. The patch preferably has adherent properties such that it can adhere to the injured or sensitive area of the body. The term patch does not require the presence of a medicament, although, as is described in more detail herein, the embodiments described herein could include such a medicament. As such, the scope of the present application should be determined by the claims.

The present disclosure generally relates to support articles. In some embodiments, the support article is a patch that, when applied, eliminates or reduces joint or muscle pain, soreness, and/or swelling and/or increases mobility and/or stability. In some embodiments, these benefits are provided, at least in part, by a strap that extends across a portion of the support article and increases the compression force of the support article on the affected area of the user.

The inventors of the present disclosure recognized that localized compression is useful in the prevention and treatment of various soft tissue symptoms or pathologies (e.g., tennis elbow, golfer's elbow, patellofemoral syndrome, chondramalacia patella, etc). The inventors of the present disclosure also realized that most existing orthopedic devices apply predominantly or solely circumferential force or targeted soft tissue areas. As such, these devices do not allow local perpendicular force adjustment to be made separately from and/or in addition to general circumferential force adjustment. This approach can cause an undesirable tourniquet effect. To provide localized compression to targeted or affected areas, the inventors of the present disclosure created a support article with a base material combined with a compression strap. When in use, the support article applies direct pressure over the affected area. Three exemplary benefits to this are as follows: 1) this applies transverse friction massage aiding in reduction of associated pain; 2) the compression also serves to apply counterforce, thereby reducing the concentration of forces on the tendon insertion point; and/or 3) where the support article is applied to the knee, direct pressure also aids in reducing the force exerted by the patella within the femoral groove, which can aid in reducing the direct contact of the underside of the patella and thereby helping to alleviate pain associated with chondromalacia patella.

In some embodiments, the support article has a shape and size tailored for a specific body area. In some embodiments, the support article can be used in any of the following exemplary body areas: IT band, hip, calf, shin, quads, hamstrings, groin, hip flexor, gluteus, outer knee, inner knee, Osgood shlatter, back of knee, front of knee, Achilles tendon, ankle, ball of foot, top of foot, arch, foot, heel, toe, finger, SI joint, low back, middle back, ribs, spine, abdominal, neck, shoulder, rotator cuff, AC joint, wrist, elbow, thumb, trapezius, bicep, and/or tricep. In some embodiments, the support article has a more general use and a single shape or design can be used in a number of different body areas.

Figure 3:
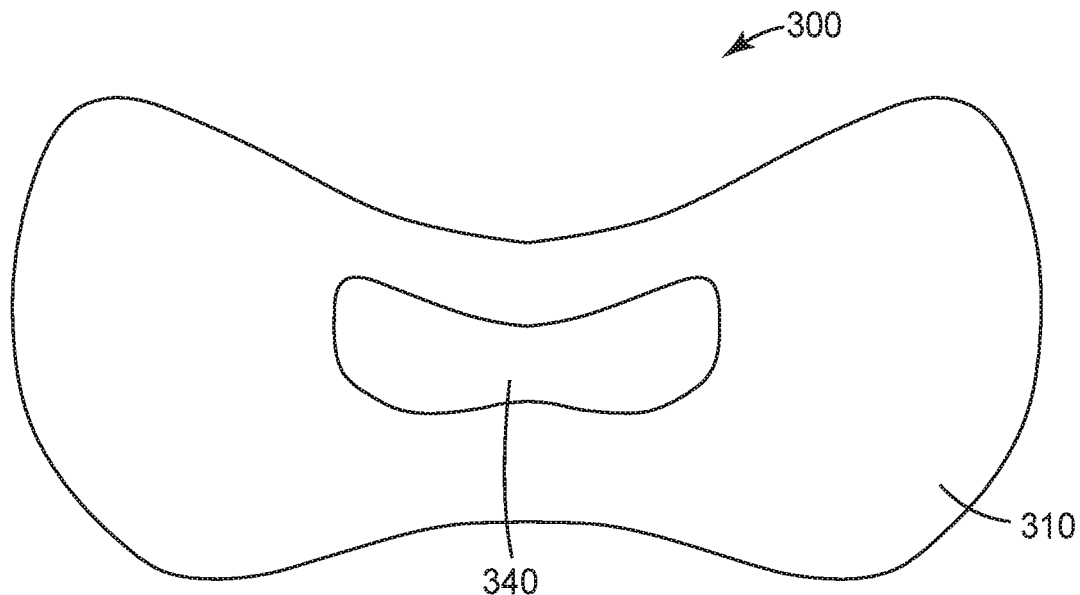
FIG. 3 is a front view of another exemplary embodiment of a support article in accordance with the teachings of the present disclosure.
Figure 4A:
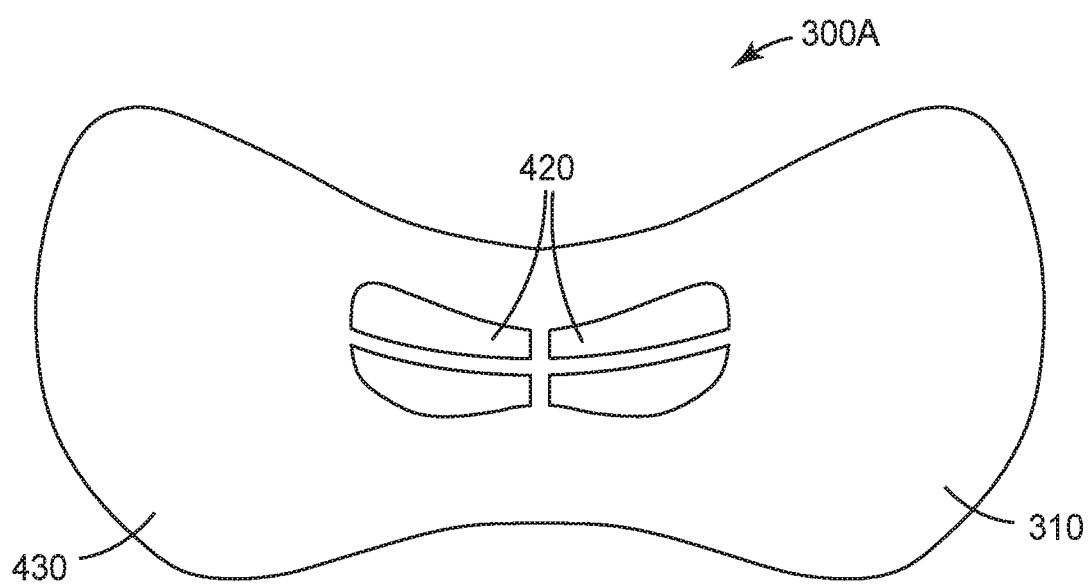
FIGS. 4A-4C are rear views of three different exemplary embodiments of support articles in accordance with the teachings herein.
Figure 4B:
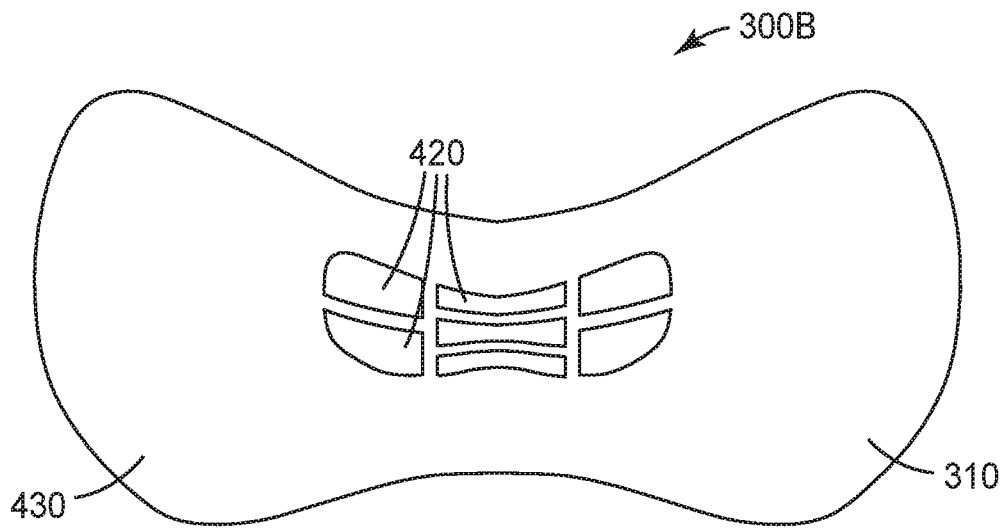
Figure 4C:
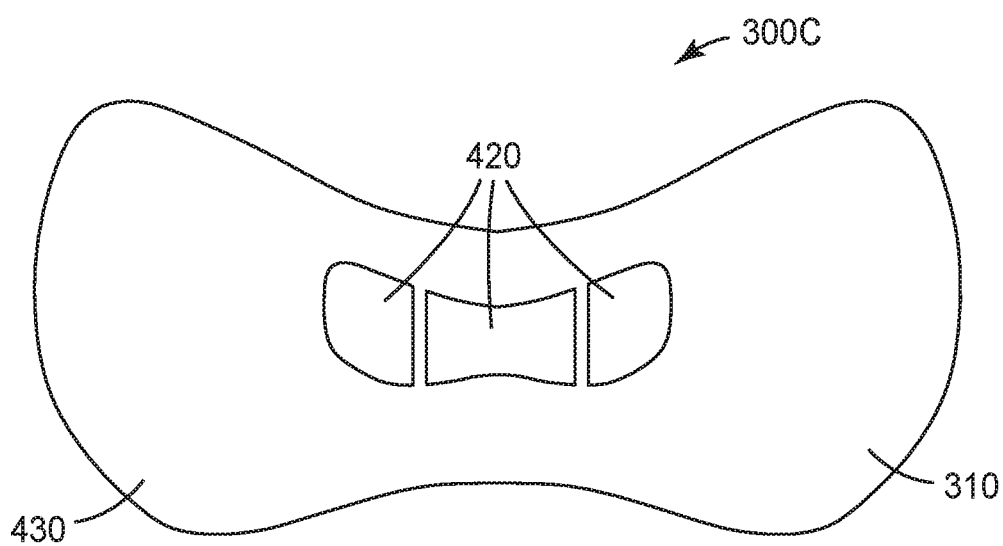
Figure 5A:
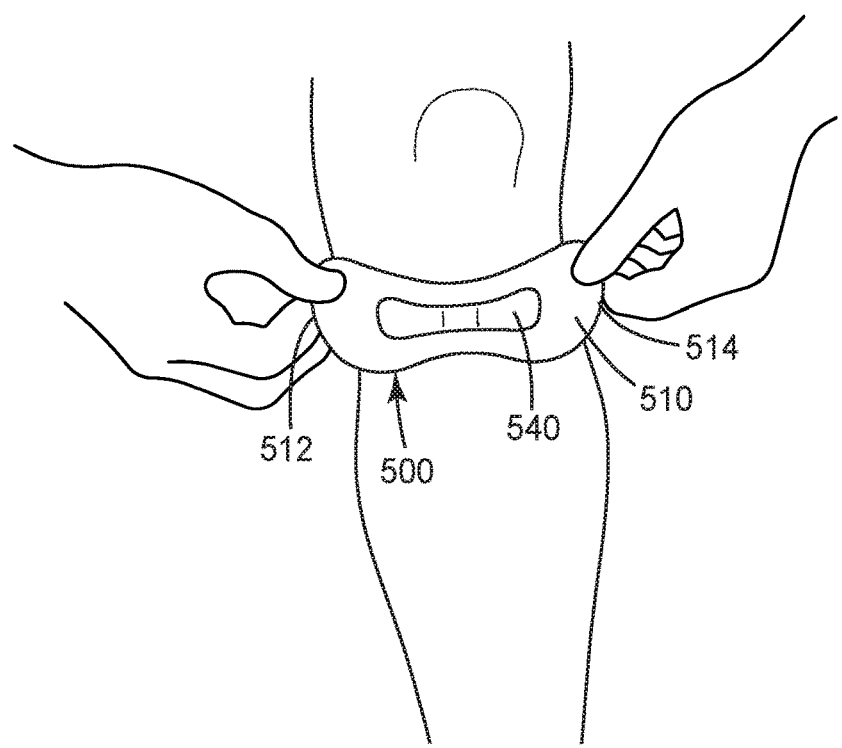
FIGS. 5A-5C are schematic drawings showing one exemplary method of applying an exemplary embodiment of a support article in accordance with the teachings of the present disclosure.
Figure 5B:
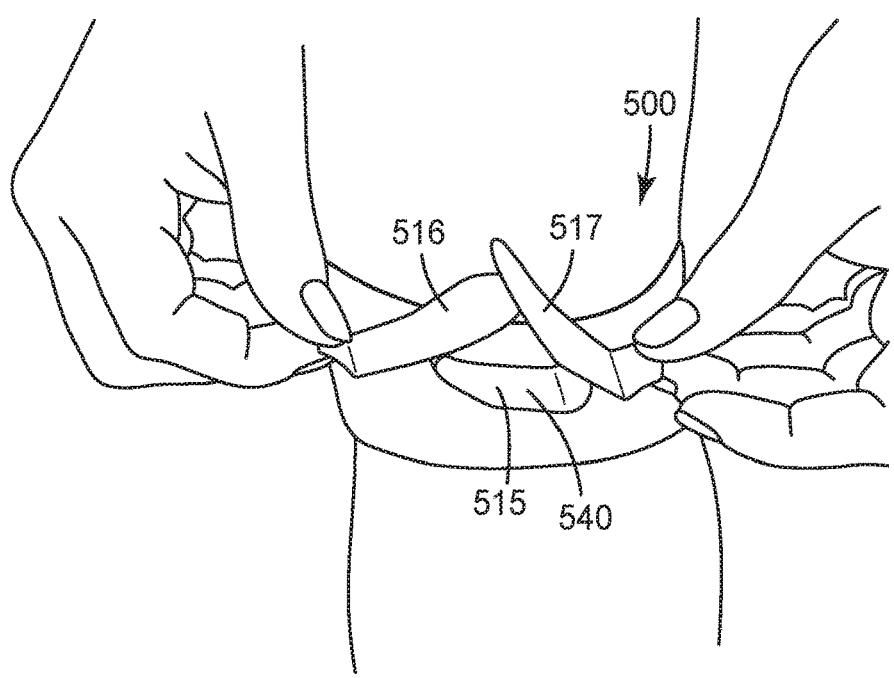
Figure 5C:
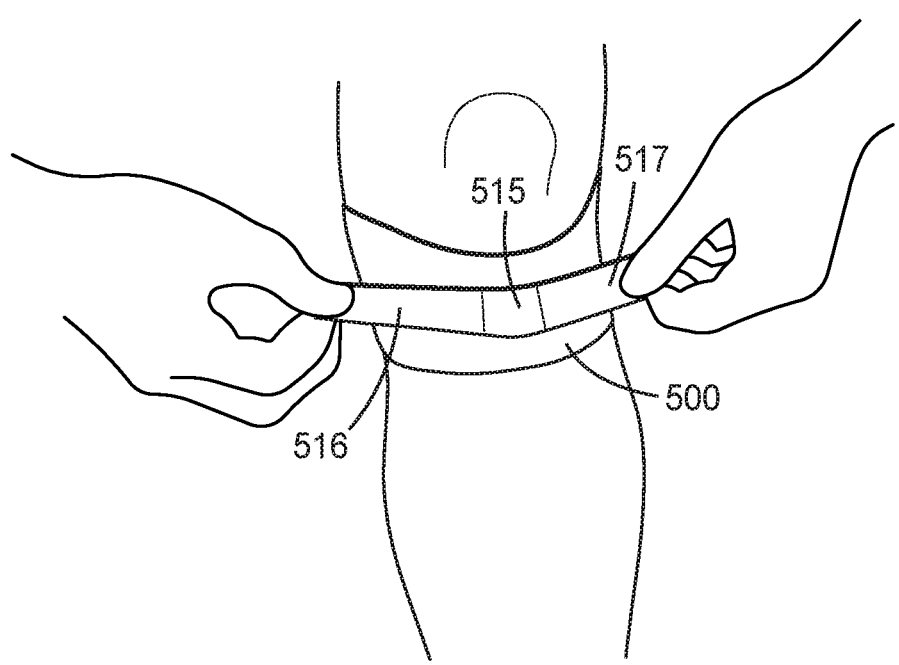

FIGS. 1-4C show various support article embodiments that can be used, for example, as knee support articles (as shown more specifically in FIGS. 5A-5C). FIGS. 1A and 1B are respective front (or top) and rear (or back or bottom) views of one exemplary embodiment of a support article in accordance with the teachings of the present disclosure. Support article 100 includes a backing 110 in the shape shown. The rear (or back or bottom) major surface of backing 110 is shown in FIG. 1B. The rear (or back or bottom) major surface of backing 110 is at least partially coated with or adjacent to an adhesive 130. Any adhesive capable of use on skin can be used, as is discussed in greater detail below.

A strap 140 is on or adjacent to the front (or top) major surface of backing 110. Strap 140 is preferably extensible such that when backing 110 is in position on a user, one or both ends of strap 140 can be extended to increase or enhance the compression force the support article 100 applies to a user's affected area. Strap 140 includes a front (or top) major surface and a back (or bottom or rear) major surface. In some embodiments, the back (or bottom or rear) major surface of the strap is at least partially coated with adhesive to permit (1) at least a portion of the strap to adhere or attach to the backing during manufacturing of the support article; and/or (2) to permit some portion of the strap to adhere to the backing or user's skin when the strap is stretched and positioned to provide compression during use of the support article. Optionally, one or more release liners can be present on the adhesive portions of condition (2) above. This permits ease of use for the user and prohibits the adhesive-coated portions of the strap from adhering to the backing before the user positions them. In some embodiments, the backing is mechanically attached to the backing in either or both of conditions (1) and (2) described above such as by the mechanical methods described herein including, for example, lamination, ultrasonic welding, hook and loop, etc.

Figure 2A:
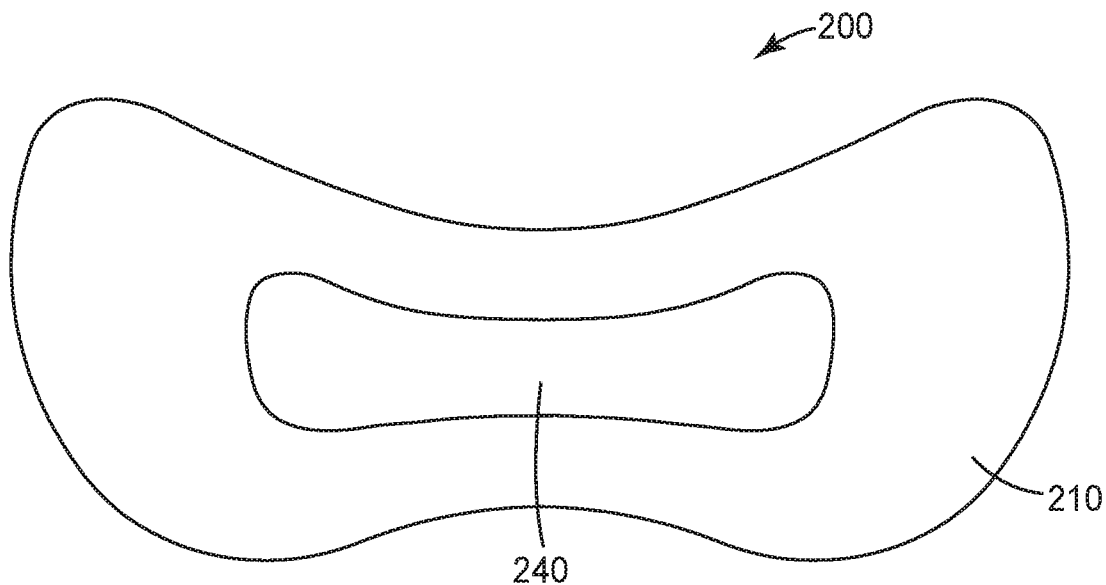
FIGS. 2A and 2B are respective front and rear views of one exemplary embodiment of a support article in accordance with the teachings of the present disclosure
Figure 2B:
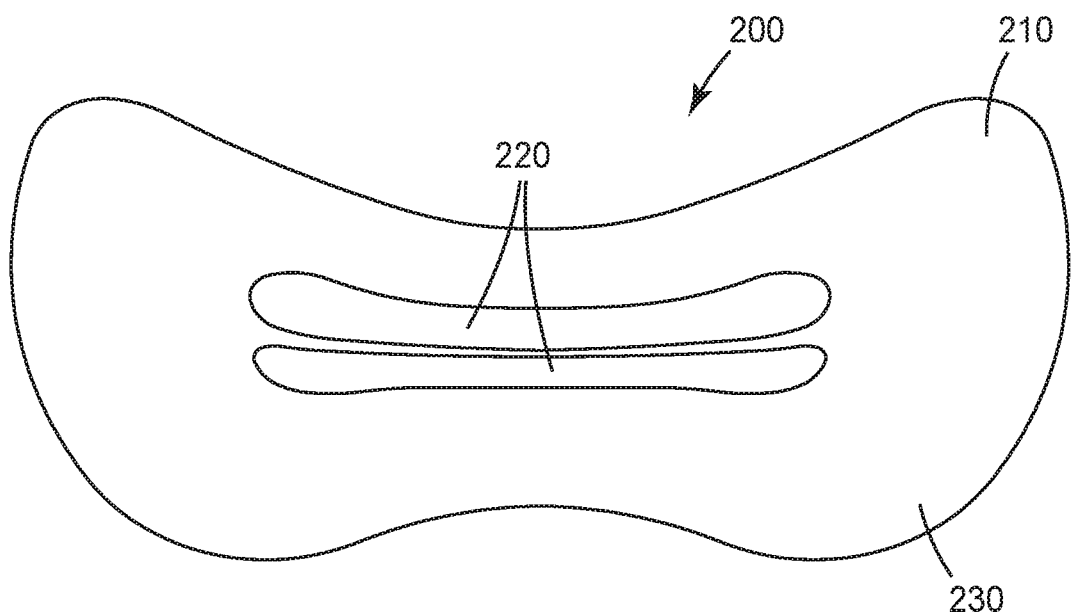

FIGS. 2A and 2B are respective front (or top) and rear (or back or bottom) views of another exemplary embodiment of a support article in accordance with the teachings of the present disclosure. The front (or top) view of support article 200 is generally the same as shown in FIG. 1A. As shown in FIG. 2B, the rear (or back or bottom) major surface of backing 210 is at least partially coated with or adjacent to an adhesive 230. Any adhesive capable of use on skin can be used, as is discussed in greater detail below. Also adhered, attached, or adjacent to the rear (or back or bottom) major surface of backing 210 are two reinforcing portions 220. Reinforcing portions 220 can further enhance the compression, stabilization, and/or support of support article 200 when in use.

FIG. 3 is a front view of another exemplary embodiment of a support article in accordance with the teachings of the present disclosure. Support article 300 includes a backing 310 in the shape shown. A strap 340 is on or adjacent to the front (or top) major surface of backing 310. Strap 340 is preferably extensible such that when backing 310 is in position on a user, one or both ends of strap 340 can be extended to increase or enhance the compression force the support article 300 applies to a user's affected area.

FIGS. 4A-4C are each a rear view of a different exemplary embodiments of support articles whose front (or top) side is shown in FIG. 3. As such, three different embodiments of a rear (or back or bottom) major surface of backing 310 of FIG. 3 are shown in each of FIGS. 4A-4C. In each of FIGS. 4A-4C, the rear (or back or bottom) major surface of backing 310 is at least partially coated with or adjacent to an adhesive 430. Any adhesive capable of use on skin can be used, as is discussed in greater detail below. Also adhered, attached, or adjacent to the rear (or back or bottom) major surface of backing 310 are one or more reinforcing portions 420 that enhance the compression, stabilization, and/or support of support article 300, 300A, 300B, or 300C when in use. FIG. 4A includes four reinforcing portions 420 in the shape and spacing generally shown. FIG. 4B includes seven reinforcing portions 420 in the shape and spacing generally shown. FIG. 4C includes three reinforcing portions 420 in the shape and spacing generally shown.

The embodiments shown in FIGS. 1-4C are merely exemplary and many changes may be made to these embodiments without departing from the scope of the present disclosure. For example, any desired shape, size, length, or thickness strap may be used. More than one strap may be used. The strap can be, for example, a one-way strap or a two-way strap. A one-way strap is a strap with one portion that can be elongated or pulled and attached or adhered to the backing or the user's skin. A two-way strap is a strap with two portions that can be elongated or pulled and attached or adhered to the backing or the user's skin. In some embodiments, the two-way strap includes a center region 515 which is pre-adhered to the backing and terminal ends 516 and 517 which include liners removable by the user, as is shown in FIGS. 5A-5C.

Any desired number, shape, size, or thickness reinforcing portion(s) may be used. Reinforcing portions need not be included. Any desired shape, size, or thickness backing may be used. Any of the backings, adhesives, and/or reinforcing portions described herein can be used. Any adhesive capable of use on skin can be used, as is discussed in greater detail herein. The reinforcing portions, where present, can be adhesively attached or adhered to the backing or can be mechanically attached or adhered to the backing, as is described in greater detail herein. An optional release liner (not shown) may be positioned adjacent to at least a portion of the adhesive and/or backing. The release liner may extend over the reinforcing portions or may have a cut out around the reinforcing portion(s). The support article positioning on the body may differ from that shown in the following figures.

FIGS. 5A-5C schematic drawings showing an exemplary method of applying an exemplary embodiment of a support article 500 in accordance with the teachings of the present disclosure. The support article can be, for example, any of those shown in FIGS. 1-4C. First, where present, a release liner can be removed from the back (or rear) side of support article 500 (not shown). The two-way strap 540 of this embodiment includes a center region 515 which is pre-adhered to the backing and terminal ends 516 and 517 which include liners removable by the user. As shown in FIG. 5A, the terminal ends 512 and 514 of support article 500 are then held taut by the user and are then applied below the user's kneecap such that support article 500 generally lays flat on the user's skin. This is often done best by letting the middle or center portion of support article 500 adhered to the user's skin (preferably adjacent to the affected area) and then slowly letting the remainder of support article 500 adhered to the user's skin, ending with terminal ends 512, 514. The user can thus control the pressure, tension, or force of the bandage by controlling the degree to which the user stretches support article 500 across the affected area. In some embodiments, terminal ends 512, 514 are repositionable against the backing and/or user's skin so that the user may adjust the pressure and/or compression as desired. As shown in FIG. 5B, once the backing is in place on the user's knee, the user partially removes the release liners (where present) from the first and second terminal ends 516 and 517 of strap 540. As shown in FIG. 5C, the user grips first and second terminal ends 516 and 517 of strap 540 and pulls them away or apart from one another to extend strap 540 along the length of support article 500. Once first and second terminal ends 516 and 517 are extended to create the desired level of pressure or compression, terminal ends 516 and 517 are pushed toward the top (or front) major surface of backing 510 and/or the user's knee or skin to adhere strap 540 to backing 510 and/or to the user's skin. Those of skill in the art will appreciate that many of the details may be changed without departing from the scope of the present disclosure. For example, instead of the user gripping and pulling both first and second terminal ends 516 and 517 at the same time, they could be separately and sequentially gripped, pulled, and adhered to the backing or user.

Figure 6:
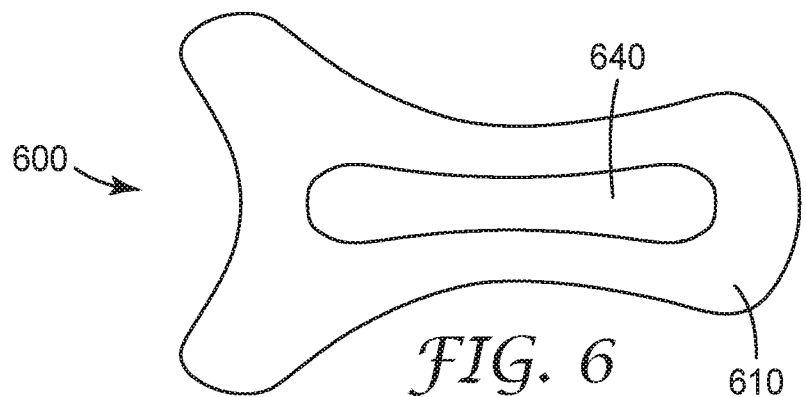
FIG. 6 is a front view of another exemplary embodiment of a support article in accordance with the teachings of the present disclosure.
Figure 7A:
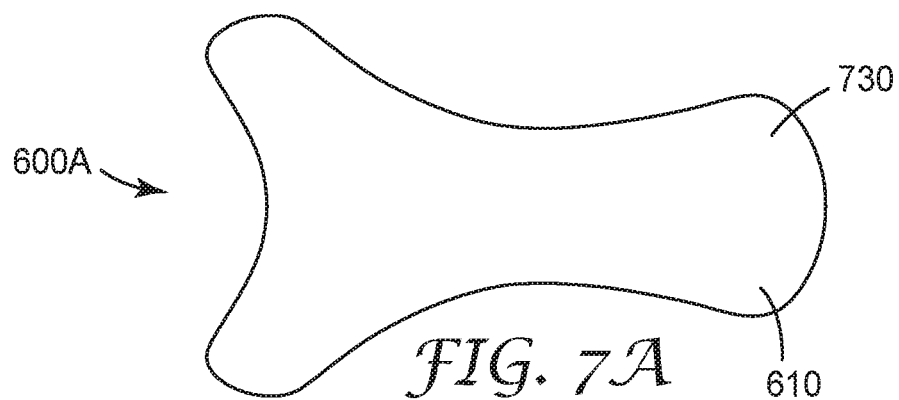
FIG. 7A-7D are rear views of four different exemplary embodiments of the support article shown in FIG. 6.
Figure 7B:
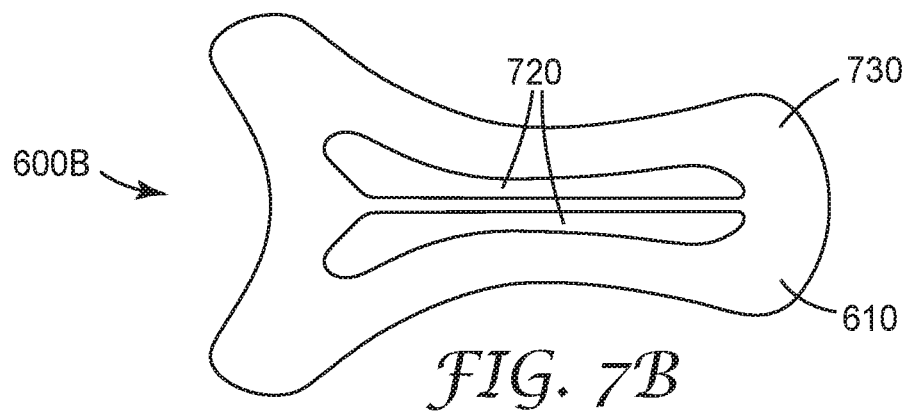
Figure 7C:
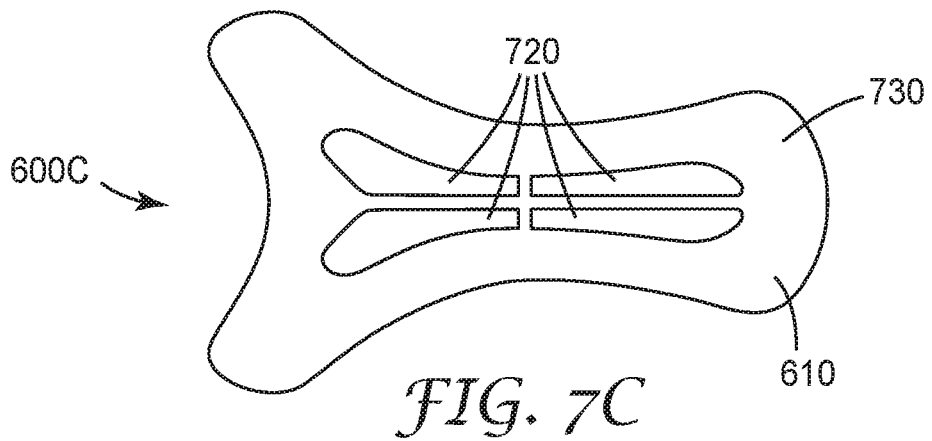
Figure 7D:
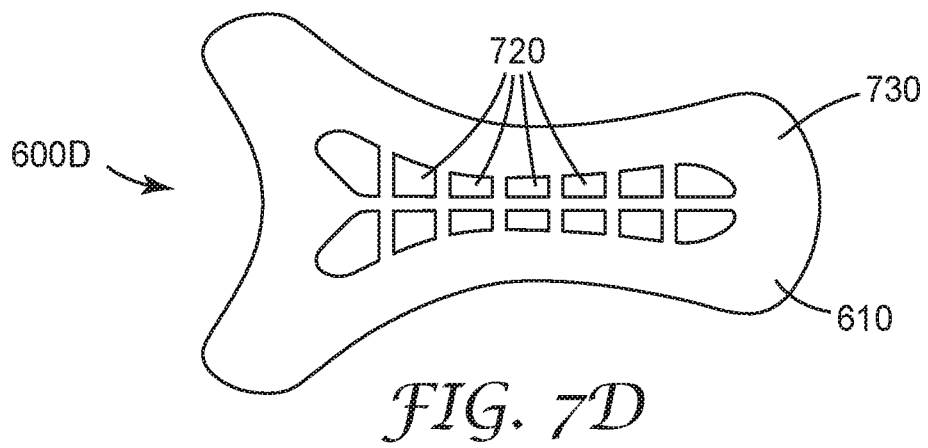
Figure 8:
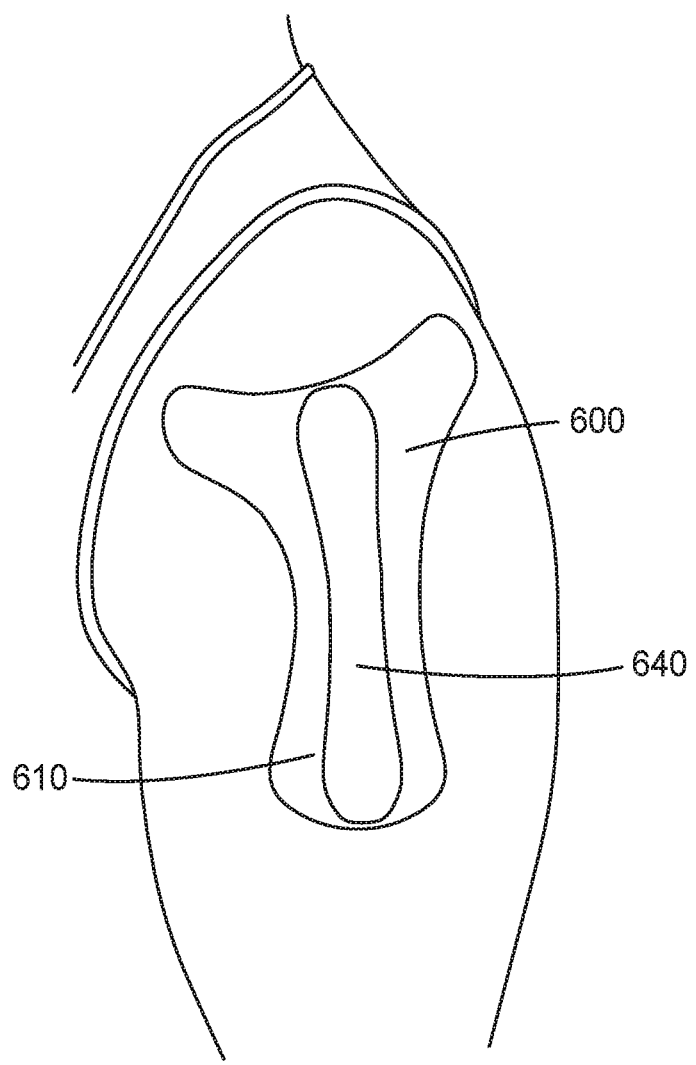
FIG. 8 is a schematic drawing of a support article of any of FIGS. 6-7D in use.

FIGS. 6-8 show various support article embodiments that can be used, for example, as shoulder support articles. FIG. 6 is a front view of another exemplary embodiment of a support article in accordance with the teachings of the present disclosure. Support article 600 includes a backing 610 in the shape shown. The shape generally includes an elongate middle portion that terminates in two wing portions. A strap 640 is on or adjacent to the front (or top) major surface of backing 610. Strap 640 is preferably extensible such that when support article 600 is in position on a user, one or both ends of strap 640 can be extended to increase or enhance the compression force the support article 600 applies to a user's affected area.

FIG. 7A-7D are rear views of four different exemplary embodiments of a support article whose front (or top) side is shown in FIG. 6. As such, four different embodiments of a rear (or back or bottom) major surface of backing 610 of FIG. 6 are shown in FIGS. 7A-7D. Support article 600A of FIG. 7A includes a back (or rear or bottom) major surface of backing 610 that is at least partially coated with or adjacent to an adhesive 730 that is capable of adhering support article 600A to the user's skin. Support article 600B of FIG. 7B also includes adhesive 730 on the back (or rear or bottom) major surface of backing 610 as shown in FIG. 7A, and also includes two reinforcing portions 720 that are generally mirror images of one another. Support article 600C of FIG. 7C also includes adhesive 730 on the back (or rear or bottom) major surface of backing 610 as shown in FIG. 7A, and also includes four reinforcing portions 720. Support article 600D of FIG. 7D is also includes adhesive 730 on the back (or rear or bottom) major surface of backing 610 as shown in FIG. 7A, but also includes fourteen reinforcing portions 720.

The embodiments shown in FIGS. 6-8 are merely exemplary and many changes may be made to these embodiments without departing from the scope of the present disclosure. For example, any desired shape, size, length, or thickness strap may be used. More than one strap may be used. The strap can be, for example, a one-way strap or a two-way strap. Any desired number, shape, size, or thickness reinforcing portion may be used. Reinforcing portions need not be included. Any desired shape, size, or thickness backing may be used. Any of the backings, adhesives, and/or reinforcing portions described herein can be used. Any adhesive capable of use on skin can be used, as is discussed in greater detail herein. The reinforcing portions, where present, can be adhesively attached or adhered to the backing or can be mechanically attached or adhered to the backing, as is described in greater detail herein. An optional release liner (not shown) may be positioned adjacent to at least a portion of the adhesive and/or backing. The release liner may extend over the reinforcing portions or may have a cut out around reinforcing portions. The support article positioning on the body may differ.

FIG. 8 is a schematic drawing of support article 600 in use on a human's shoulder. In this embodiment, the elongate body portion is applied on the user's upper arm such that the area where the elongate body portion contacts the first and second wing portions is generally over or adjacent to the shoulder joint area. Each of the first and second wing portions extend anteriorly and posteriorly (or toward the user's front and toward the user's back, respectively) from the user's shoulder region. The wing portions help to anchor the support article over the shoulder area. Strap 640 is a two-way strap whose terminal ends extend toward the terminal ends or sides of backing 610 when in use. In an alternative embodiment, the terminal ends of the strap can extend beyond or past the terminal ends of the backing when in use. This provides compression and/or support to the user's general shoulder area.

Figure 9A:
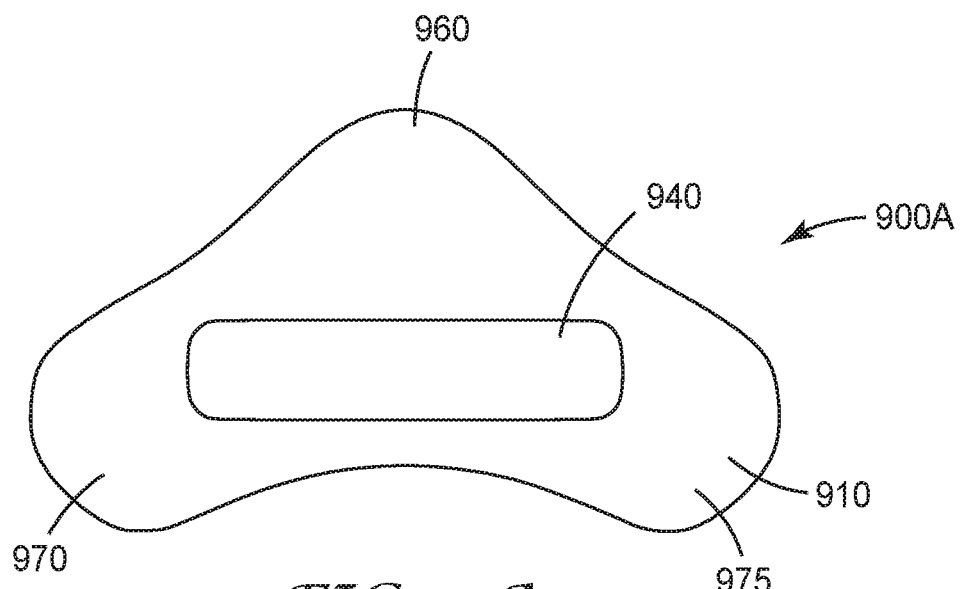
FIGS. 9A and 9B are respective front and rear views of another exemplary embodiment of a support article in accordance with the teachings of the present disclosure.
Figure 9B:
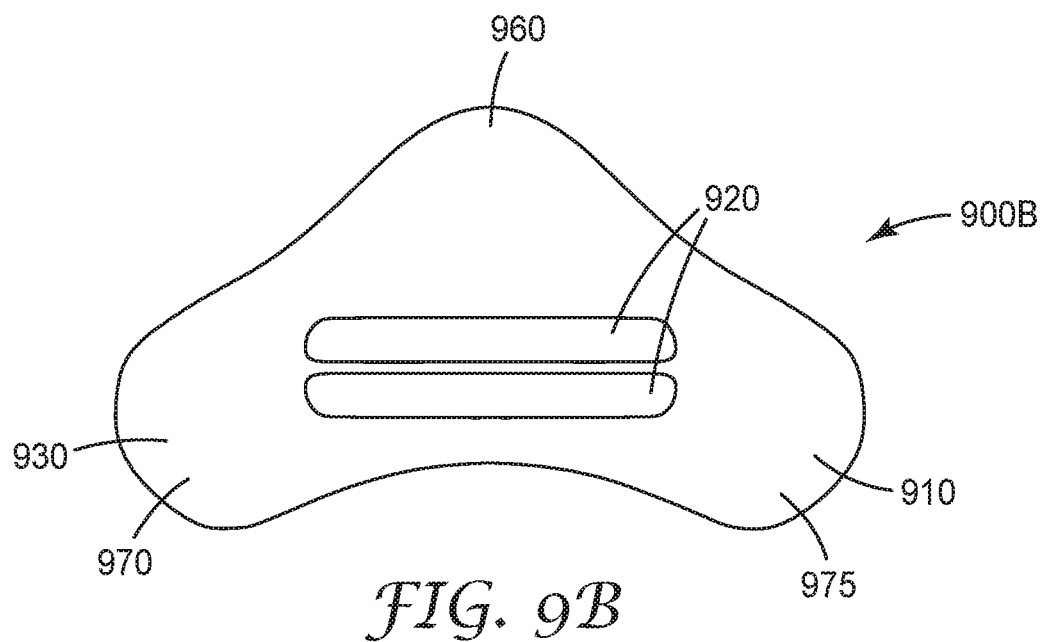

FIGS. 9-11 show various support article embodiments that can be used, for example, as elbow support articles. FIGS. 9A and 9B are respective front and rear views of an exemplary embodiment of a support article in accordance with the teachings of the present disclosure. As shown in FIG. 9A, support article 900 includes a backing 910 in the shape shown. The exemplary shape shown is generally triangular with an apex portion 960 and two side (or wing) portions 970, 975 (also referred to as first and second side or wing portions). A strap 940 is on or adjacent to the front (or top) major surface of backing 910. Strap 940 is preferably extensible such that when backing 910 is in position on a user, one or both ends of strap 940 can be extended to increase or enhance the compression force the support article 900 applies to a user's affected area. As shown in FIG. 9B, the back (or rear or bottom) major surface of backing 910 includes two reinforcing portions 920 with identical or similar shapes spaced apart from one another. Also, the back (or rear or bottom) major surface of backing 910 is at least partially coated with or adjacent to an adhesive 930 that is capable of adhering support article 900 to the user's skin and which, in some embodiments, may also adhere the one or more reinforcing portions 920 to backing 910.

Figure 10A:
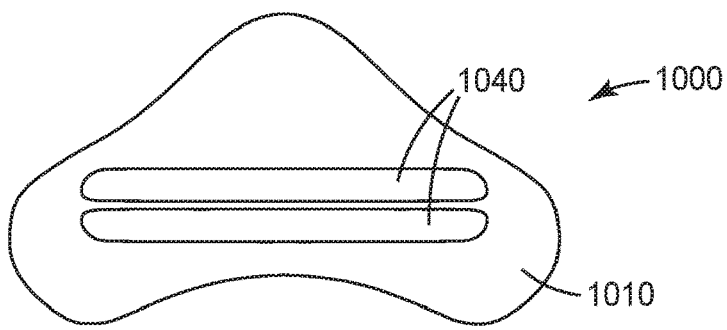
FIG. 10A is a front view of an exemplary embodiment of a support article in accordance with the teachings herein.

FIG. 10A is a front view of an exemplary embodiment of a support article in accordance with the teachings herein. Support article 1000 of FIG. 10A is similar to support article 900 of FIG. 9A except that it includes two straps 1040. In this specific embodiment, straps 1040 are mirror images of one another and are spaced apart from one another, but any strap size, shape, or spacing may be used.

Figure 10B:
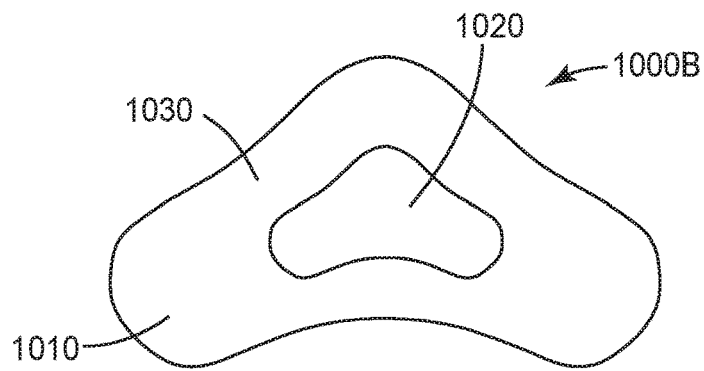
FIGS. 10B-10D are rear views of three different exemplary embodiments of the support article shown in FIG. 10A.
Figure 10C:
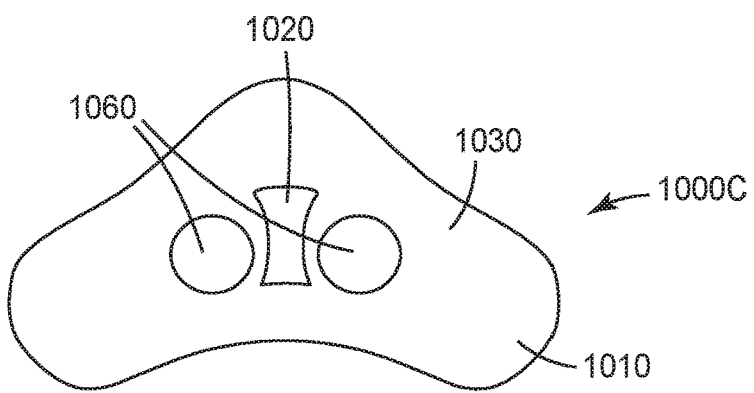
Figure 10D:
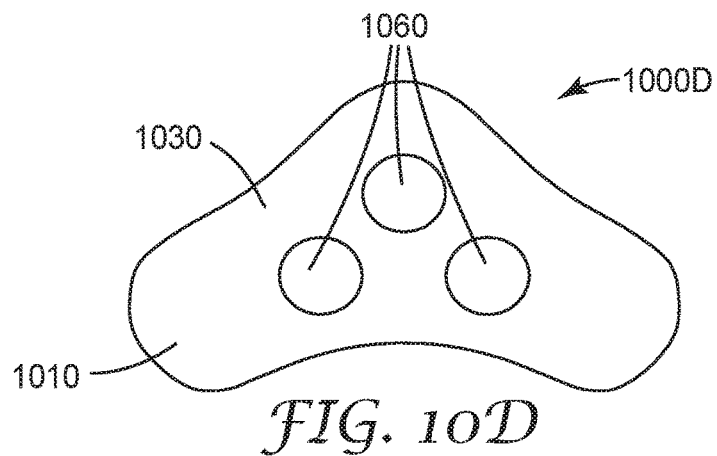

FIGS. 10B-10D are rear views of three different exemplary embodiments of a support article whose front (or top) major surface is shown in FIG. 9A or 10A. All of the support articles 1000B, 1000C, and 1000D include an adhesive 1030 on the rear (or back or bottom) major surface of backing 1010. Support article 1000B of FIG. 10B further includes a single reinforcing portion whose shape generally mimics, mirrors, or follows the shape of backing 1010. Support article 1000C of FIG. 10C includes a reinforcing portion 1020 between two bumps. Support article 1000D of FIG. 10D further includes three identically or similarly shaped and sized bumps 1060. Bumps 1060 provide enhanced, targeted point pressure and are described in greater detail below. In some embodiments, the support articles include a bump, bumper, or projection that extends from the backing toward the affected area of the user and provides targeted, localized contact and/or pressure to the affected area. In some embodiments, the bump, bumper, or projection is a 3M Bumpon™ device made by 3M Company of St. Paul, Minn.

FIG. 11 is a schematic drawing of support article 900 in use on a human's elbow. In this specific embodiment, apex portion 960 is positioned toward the user's upper arm and first and second side or wing portions 970, 975 extend around the upper portion of the user's forearm (or lower arm). Notably, this is merely an exemplary positioning embodiment for the support article and others may be used. Strap 940 extends across the support article and adhere to backing 910 when in use (not shown). In some embodiments, strap 940 extends across and past backing 910 and adhere to the user's skin when in use (not shown). In this way, enhanced compression is provided to the user's general elbow area.

The embodiments shown in FIGS. 9-11 are merely exemplary and many changes may be made to these embodiments without departing from the scope of the present disclosure. For example, any desired shape, size, length, or thickness strap may be used. More than one strap may be used. The strap can be, for example, one-way or two-way. Any desired number, shape, size, or thickness reinforcing portion may be used. Reinforcing portions need not be included. Any desired number, shape, size, or thickness bump may be used. Bumps need not be included. Any desired shape, size, or thickness backing may be used. Any of the backings, adhesives, and/or reinforcing portions described herein can be used. Any adhesive capable of use on skin can be used, as is discussed in greater detail herein. The reinforcing portions, where present, can be adhesively attached or adhered to the backing or can be mechanically attached or adhered to the backing, as is described in greater detail herein. An optional release liner (not shown) may be positioned adjacent to at least a portion of the adhesive and/or backing. The release liner may extend over the reinforcing portions or may have a cut out around reinforcing portions. The support article positioning on the body may differ.

FIGS. 12A and 12B are respective front and rear views of an exemplary embodiment of a support article in accordance with the teachings of the present disclosure. As shown in FIG. 12A, support article 1200 includes a backing 1210 in the shape shown. The shape generally includes a top portion 1260 that is slightly wider than a lower portion 1265. A strap 1240 is on or adjacent to the front (or top) major surface of backing 1210. Strap 1240 is preferably extensible such that when backing 1210 is in position on a user, one or both ends of strap 1240 can be extended to increase or enhance the compression force the support article 1200 applies to a user's affected area. As shown in FIG. 12B, back (or rear or bottom) major surface of backing 1210 is at least partially coated with or adjacent to an adhesive 1230 that is capable of adhering the support article to the user's skin and which, in some embodiments, may also adhere the one or more reinforcing portions 1220 (where present) to backing 1210. The back (or rear or bottom) major surface of backing 1210 also includes a first reinforcing portion 1220 on top of which are attached, adhered, stacked, or positioned two second reinforcing portions 1222. One benefit or advantage of having layered or stacked reinforcing portions is that the points where the reinforcing portions are layered or stacked can provide increased and/or differential compression and/or pressure. This can also provide, for example, one or more targeted pressure points, which can assist in pain and/or swelling reduction. In an alternative embodiment, second reinforcing portions 1222 can be bumps.

In some embodiments, first and second reinforcing portions 1220, 1222 are adhered or attached to the backing at the time the user purchases the support article and/or during manufacturing of the support article. In some alternative embodiments, second reinforcing portion(s) 1222 are not attached or adhered to the support article but are instead provided or sold separately. In such embodiments, the second reinforcing portion(s) could comprise a backing (any backing described herein) attached or adhered to a reinforcing portion (any reinforcing portion described herein attached or adhered using any method or attachment means or mechanism described herein) or merely a reinforcing portion. The uppermost (or exposed) surface of the reinforcing portion (in either implementation) could be coated (at least partially) with adhesive capable of allowing the second reinforcing portion to adhere to the user. The user could then adhere one or more second (or separate) reinforcing portions directly to the injured, swollen, impacted, or affected area. After doing so, the user would then apply the support article over and adjacent to the second (or separate) reinforcing portions.

These embodiments that include one or more second reinforcing portions may permit the application of maximum pressure to the injured, swollen, impacted, or affected area. These embodiments could also provide targeted, point pressure as needed and at the user's option. These embodiments could also provide differential pressure (greater pressure in the areas with the one or more second (or separate) reinforcing portions than the pressure under the support article) as needed and at the user's option. These embodiments could also provide areas or targeted compression where the second (or separate) reinforcing portions were positioned and areas of tape-like lift in areas where the support article was located. These embodiments could also provide ease in application in areas of the body where correct positioning can be challenging to achieve.

The embodiments shown are merely exemplary and many changes may be made without departing from the scope of the present disclosure. For example, the support article may additionally include one or more of third, fourth, firth, etc. reinforcing portions. It can include only a single second reinforcing portion or more than the two second reinforcing portions shown. These can be part of the support article at the time of manufacturing and/or purchase or can be separate. In instances where they are separate, they can be applied by the user separate from the support article. In such instances, they may become part of the support article once the user applies them and they all adhere, attach, or are placed adjacent to one another. For purposes of clarity, multiple reinforcing portions (spaced apart or stacked or layered on each other) may be used in any of the embodiments or implementations described herein.

Figure 13A:
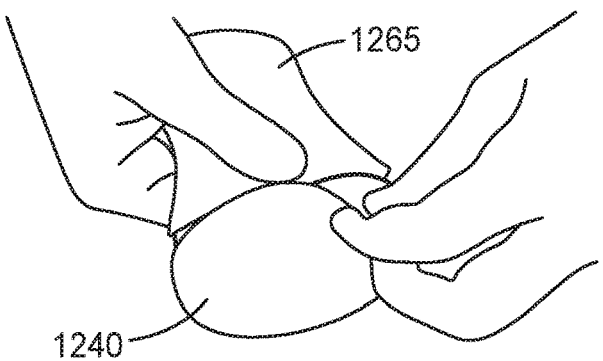
FIGS. 13A-13D are schematic drawings showing one exemplary method of applying an exemplary embodiment of a support article in accordance with the teachings of the present disclosure.
Figure 13B:
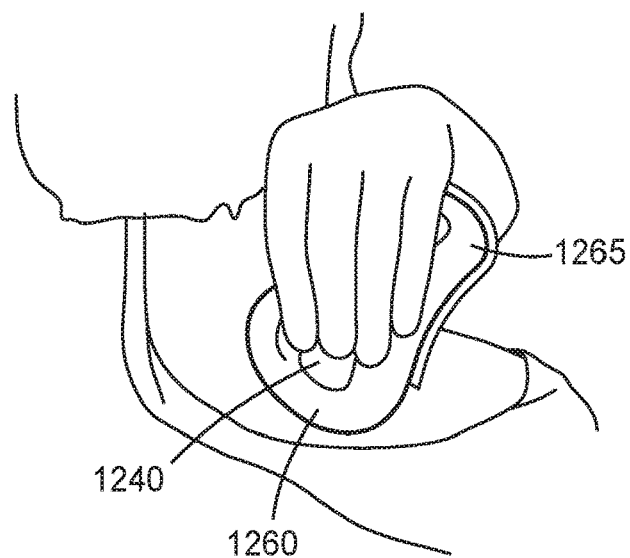
Figure 13C:
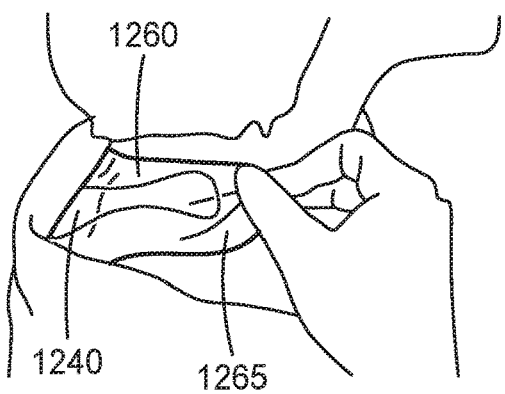
Figure 13D:
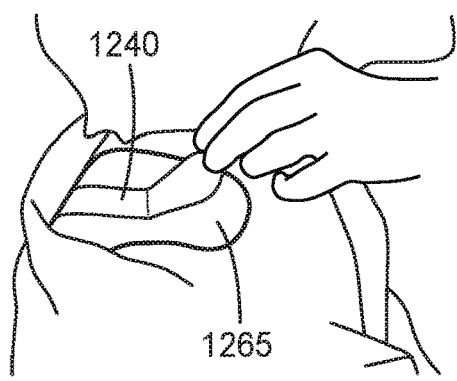

FIGS. 13A-13D schematically show the support article 1200 during application and in use on a human's trapezius. FIG. 13A shows removal of at least some of the release liner (where present). In this exemplary embodiment, the support article includes multiple, separately cut release liners. The use of separately cut release liners facilitates easy application of the support article. In the specific embodiment shown in FIG. 13A, a portion of the release liner that corresponds to top portion 1260 of support article 1200 is removed. FIG. 13B shows placement of top portion 1260 of support article 1200, whose release liner was removed, adjacent to the trapezius area of the user. In some embodiments, the support article is preferably positioned such that the reinforcing portion 1220 is adjacent to a sore, injured, or affected area. This placement ensures that the maximal pressure or compression provided by support article 1200 is applied to the sore, injured, or affected area to maximize reduction in pain, increased blood flow, decreased swelling, etc. in that area. After placement, the user may press the applied portion of the support article onto the skin to ensure a good fit and/or adherence. Next, but not shown, the user removes another portion of the release liner from support article 1200. In this specific exemplary embodiment, a portion of the release liner that corresponds to bottom or lower portion 1265 of support article 1200 is removed. FIG. 13C shows placement of bottom portion 1265 of support article 1200, whose release liner was removed, adjacent to the trapezius area of the user. In FIG. 13D, the user is shown pulling one-way strap 1240 to its desired length. Next, the user will attach the extended strap to the backing and/or user's skin (not shown).

The embodiments shown in FIGS. 12-13 are merely exemplary and many changes may be made to these embodiments without departing from the scope of the present disclosure. For example, any desired shape, size, length, or thickness strap may be used. Multiple straps can be used. A one-way or two-way strap can be used. Any desired number, shape, size, or thickness reinforcing portion may be used. Reinforcing portions need not be included. Any desired number, shape, size, or thickness of second reinforcing portions may be used. Any desired shape, size, or thickness backing may be used. One or more bumps can be used. Any of the backings, adhesives, and/or reinforcing portions described herein can be used. Any adhesive capable of use on skin can be used, as is discussed in greater detail herein. The reinforcing portions, where present, can be adhesively attached or adhered to the backing or can be mechanically attached or adhered to the backing, as is described in greater detail herein. The second reinforcing portions can be separate from the backing and/or support article or can be attached, adhered, or adjacent thereto. An optional release liner (not shown) may be positioned adjacent to at least a portion of the adhesive and/or backing. The release liner may extend over the reinforcing portions or may have a cut out around reinforcing portions. The support article positioning on the body may differ. The method of applying the support article may differ.

Figure 14A:
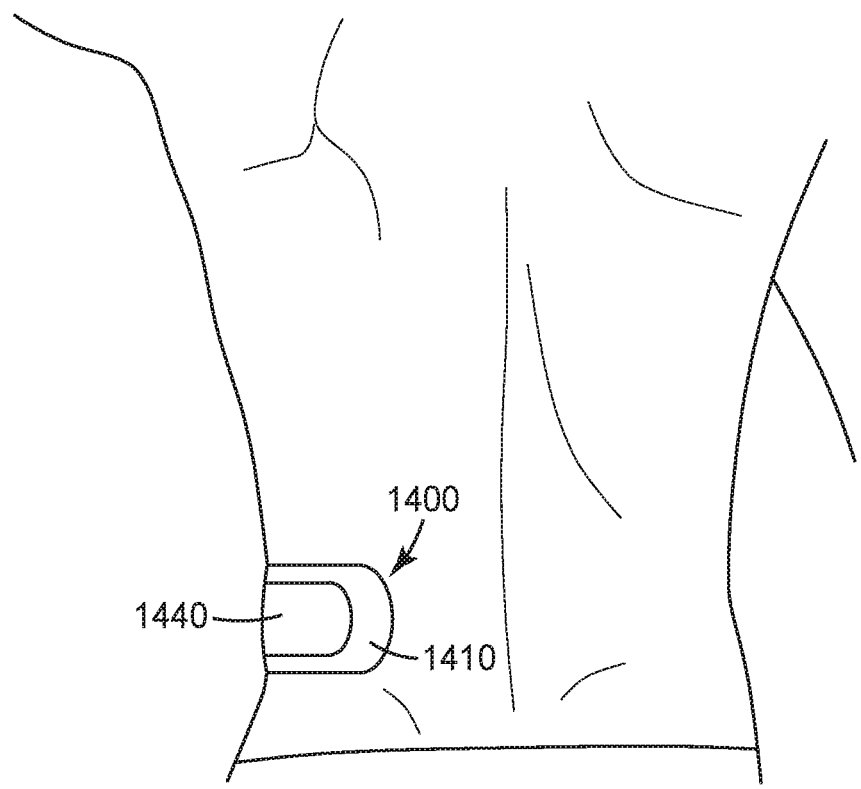
FIGS. 14A and 14B are respective front and rear views of another exemplary embodiment of a support article in accordance with the teachings of the present disclosure.
Figure 14B:
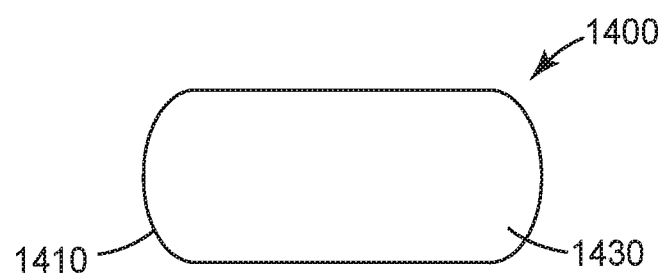

FIGS. 14A and 14B show an exemplary support article embodiment that can be used, for example, as waist/back support article. FIGS. 14A and 14B respectively show the front (or top) and rear (or bottom or back) views of an exemplary embodiment of a support article in accordance with the teachings of the present disclosure. Support article 1400 includes backing 1410 in the shape shown. The exemplary shape shown is generally a rounded rectangle or stadium shape. The rear surface of support article 1400 is coated with or adjacent to adhesive 1430. Reinforcing portion 1420 is adhered or attached to at least a portion of the rear (or back or bottom) major surface of backing 1910. In this exemplary embodiment, reinforcing portion 1420 is generally rectangularly shaped and/or has a shape that mimics or follows the general shape of backing 1410. Back (or rear or bottom) major surface of backing 1410 is at least partially coated with or adjacent to an adhesive 1430 that will adhere the support article to the users skin and which, in some embodiments, may also adhere the one or more reinforcing portions 1420 to backing 1410. FIG. 14A schematically shows support article 1900 in use on a human's waist/back.

Backing:

The backing can be any acceptable backing layer. The backing can be a single layer or multilayer. In some embodiments, the backing layer is a nonwoven layer. In some embodiments, the backing is at least one of a polyurethane film, a polyethylene film, a polypropylene film, a PVC film, a nonwoven material (e.g. an elastic nonwoven fabric), and/or a woven material. Some commercially available exemplary backings include Dureflex® and Platilon® sold or made by Covestro LLC, South Deerfield, Mass.; 3M™ Tegaderm™ sold or made by 3M Company, Maplewood, Minn.; Sontara® sold or made by Jacob Holm & Sons AG, Basel, Switzerland; HUATAO-020 sold or made by Huatao Group, Shijiazhuang, China; and PA2B sold or made by Hollingsworth & Vose, East Walpole, Mass.

Some exemplary suitable nonwoven article backings can be formed as melt blown microfiber webs using the apparatus discussed, for example, in Wente, Van A., "Superfine Thermoplastic Fibers", Industrial Engineering Chemistry, Vol. 48, pages 1342-1346, Wente, Van A. et al., "Manufacture of Superfine Organic Fibers", Report No. 4364 of the Navel Research Laboratories, published May 25, 1954, and in U.S. Pat. Nos. 3,849,241; 3,825,379, all of which are incorporated in their entirety herein. These microfine fibers are termed melt blown fibers or blown microfibers (BMF) and are generally substantially continuous and form into a coherent web between the exit die orifice and a collecting surface by entanglement of the microfibers due in part to the turbulent airstream in which the fibers are entrained. Other conventional melt spinning type processes, such as spunbond processes where the fibers are collected in a web form immediately upon fiber formation, can also be used to form the nonwoven article backing. In some embodiments, the fibers are 100 microns or less in diameter when formed by melt spinning type processes, preferably 50 microns or less. The multicomponent fibers, if formed by the melt blown process, can be produced as described in U.S. Pat. No. 5,176,952 (Joseph et al); U.S. Pat. No. 5,232,770 (Joseph); U.S. Pat. No. 5,238,733 (Joseph et al); U.S. Pat. No. 5,258,220 (Joseph); or U.S. Pat. No. 5,248,455 (Joseph et al), each of which is incorporated by reference herein in its entirety. The multicomponent fiber can also be produced by a spunbond process as are disclosed in U.S. Pat. No. 5,695,868 (McCormack); U.S. Pat. No. 5,336,552 (Strack et al); U.S. Pat. No. 5,545,464 (Stokes); U.S. Pat. Nos. 5,382,400; 5,512,358 (Shawyer et al); or U.S. Pat. No. 5,498,463 (McDowall et al), each of which is incorporated by reference herein in its entirety.

In some embodiments, the backing layer includes conjugate multicomponent melt spun fibers. For example, the backing layer can be any of the backing layers described in, for example, U.S. Pat. No. 6,107,219 (Joseph et al.), the entirety of which is incorporated by reference herein. The conjugate multicomponent melt spun fibers used to form the nonwoven backing can be, for example, polymeric. In some embodiments, the fibers are organic polymeric materials. Some exemplary suitable materials for use in forming conjugate multicomponent fibers include polyolefins, polyesters, polyalkylenes, polyamides, polystyrenes, polyarylsulfones, polydienes or polyurethanes. These materials are preferably extensible or slightly elastomeric, but could be elastomeric. In some embodiments, extensible or slightly elastomeric polyurethanes may be preferred (e.g., "MORTHANE" PS 440-200 resin available from Morton Thiokol Corp. also known as "IROGRAN" PS440-200 from Huntsman); and polyolefins such as polyethylenes, polypropylenes, ethylene-propylene copolymers, ethylene/vinyl acetate copolymers, or metallocene-type polyethylenes having a density of greater than 0.87 grams/cm$^3$. Other suitable elastomeric materials include metallocene-type polyethylene copolymers (apparent density less than 0.87 grams/cm$^3$); polyolefin elastomers (e.g., ethylene/propylene/diene elastomers); A-B block copolymers, as described above, having A blocks formed of poly (vinyl arenes) such as polystyrene and B blocks formed of conjugated dienes such as isoprene, butadiene, or hydrogenated versions thereof (e.g., "KRATON" elastomers available from Kraton Co.); polyetheresters (such as "ARNITEL", available from DSM); or polyether block amides (such as "PEBAX", available from Atochem Co.). Blends of elastomers, blends of nonelastomers or blends of both elastomers and nonelastomers can also be used.

In some embodiments, the conjugate multicomponent melt spun fibers having a diameter of no greater than about 10 microns. In some embodiments, the conjugate multicomponent melt spun fibers have a diameter up to about 50 microns or more (these are typically fibers prepared using a melt-blown process). In some embodiments, fibers having a diameter of up to about 100 microns can be prepared (these are typically fibers prepared using a spun bond process).

In some embodiments, the nonwoven backing includes additional fibers, such as, for example, other melt spun fibers, staple fibers (including inorganic and organic fibers, such as thermoplastic fibers, carbon fibers, glass fibers, or mineral fibers), organic binder fibers, and/or fibers of different polymers. Alternatively, other polymer materials can be simultaneously melt processed with the multicomponent fibers of the present invention to form webs containing more than one type of melt processed fiber, preferably, melt blown microfiber. Webs having more than one type of fiber are referred to herein as having commingled constructions. In commingled constructions, the various types of fibers can be intimately mixed forming a substantially uniform cross-section, or they can be in separate layers. The web properties can be varied by the number of different fibers used, the number of layers or regions employed, and the layer or region arrangement. Other materials, such as surfactants or binders can also be incorporated into the web before, during, or after its collection, such as by the use of a spray jet.

In some embodiments, the fibers forming the nonwoven article backing are intimately entangled each with the other in the form of a coherent breathable fibrous nonwoven article backing.

In some embodiments, the backing layer is breathable and/or porous. In some embodiments, the backing layer is highly breathable and/or porous, making the support article comfortable to wear and/or to minimize or prevent itching, irritation, or undesirable skin reactions. In some embodiments, the backing layer allows for moisture release. The more porous the backing layer, the better the backing layer will release moisture caused by sweating or being worn in water or humid environments. In some embodiments, the backing layer has a breathability and/porosity of between about 3 and about 12 mm $H_2O$ measured using the pressure drop test. In some embodiments, the backing layer has a breathability and/porosity of between about 4 and about 12 mm $H_2O$ measured using the pressure drop test. In some embodiments, the backing layer has a breathability and/porosity of at least about 3 mm $H_2O$ measured using the pressure drop test. In some embodiments, the backing layer has a breathability of at least about 5 mm $H_2O$ measured using the pressure drop test described herein.

In some embodiments, the backing has a weight of between about 25 gsm to about 300 gsm. In some embodiments, the backing has a weight of between about 120 gsm to about 160 gsm.

In some embodiments, the backing has a cross-directional tensile strength of between about 4 lbf (17.8 N) and about 9 lbf (40.0 N). In some embodiments, the backing has a cross-directional tensile strength of between about 5 lbf (22.2 N) and about 8 lbf (35.6 N). In some embodiments, the backing has a cross-directional tensile strength of between about 6 lbf (26.7 N) and about 7 lbf (31.1 N). In some embodiments, the backing has a cross-directional tensile strength of greater than about 4 lbf (17.8 N). In some embodiments, the backing has a cross-directional tensile strength of greater than about 5 lbf (22.2 N). In some embodiments, the backing has a cross-directional tensile strength of less than about 9 lbf (40.0 N). In some embodiments, the backing has a cross-directional tensile strength of less than about 8 lbf (35.6 N).

In some embodiments, the backing has a machine-directional tensile strength of between about 5 lbf (22.2 N) and about 10 lbf (44.5 N). In some embodiments, the backing has a machine-directional tensile strength of between about 6 lbf (26.7 N) and about 9 lbf (40.0 N). In some embodiments, the backing has a machine-directional tensile strength of between about 7 lbf (31.1 N) and about 8 lbf (35.6 N). In some embodiments, the backing has a machine-directional tensile strength of greater than about 5 lbf (22.2 N). In some embodiments, the backing has a machine-directional tensile strength of greater than about 6 lbf (26.7 N). In some embodiments, the backing has a machine-directional tensile strength of less than about 10 lbf (44.5 N). In some embodiments, the backing has a machine-directional tensile strength of less than about 9 lbf (40.0 N). Tensile strength was measured as described herein.

In some embodiments, the backing has a cross-directional elongation at break of about 900%. In some embodiments, the backing has a cross-directional elongation at break of between about 600% and about 900%, or between about 600% and about 800%. Elongation at break was measured as described herein.

In some embodiments, the backing has a machine-directional elongation at break of about 1000%. In some embodiments, the backing has a machine-directional elongation of between about 350% and about 1000%, or between about 450% and about 550%. Elongation was measured as described herein.

The backing can have any suitable thickness. In some embodiments, the backing has a thickness of between about 0.01 cm (3.94 mil) and about 1 cm (393 mil). In some embodiments, the backing has a thickness of at least 0.01 cm (3.94 mil). In some embodiments, the backing has a thickness of no greater than about 0.5 cm (197 mil), or about 0.4 cm (157 mil), or about 0.3 cm (118 mil), or about 0.2 cm (79 mil), or about 0.1 cm (39 mil). In some embodiments, the backing has a thickness of less than about 1 mil (0.0025 cm), or less than 0.75 mil (0.0019 cm), or less than 0.5 mil (0.0127 cm).

Adhesive

Adhesives used in the present disclosure can include at least two adhesives: (1) the adhesive used to adhere the support article to the user (located on the rear (or bottom or back) side of the backing) or a separately sold or provided reinforcing portion or bump that the user applies to himself/herself; and (2) the adhesive (where used) used to adhere the reinforcing portion(s) and/or the strap to the backing (or multiple reinforcing portions or bumps to another other). In some embodiments, these two adhesives are the same. In some embodiments, these two adhesives differ. In embodiments including both reinforcing portions and one or more straps, differing attachment or adhesion means can be used, or the same means can be used. In some embodiments, the reinforcing portion(s) and/or strap(s) are attached to the backing using non-adhesive means, in which case the second adhesive would not be present. Some exemplary non-adhesive means of attachment include lamination, ultrasonic welding, hook and loop, etc. Each of these adhesives will be described in greater detail below.

Adhesives Used to Adhere the Backing or Support Article to the User

Any adhesive capable of use on skin may be used on the rear (or back or bottom) side of the backing to adhere the backing to the user. Selection of a desired adhesive to adhere the backing to the user may be based on various factors including, for example, the region of the body on which the support article is meant to be used, the skin sensitivity profile of the end user, etc. Some exemplary adhesives include those described in, for example, U.S. Pat. No. 6,107,219 (Joseph et al.), U.S. Pat. No. 6,703,120 (Ko et al.); U.S. Pat. No. 7,407,709 (Zhou et al.); U.S. Pat. No. 7,807,268 (Zhou et al.); U.S. Pat. No. 9,359,529 (Liu et al.); U.S. Pat. No. 8,541,481 (Determan et al.); U.S. Pat. No. 9,017,771 (Determan et al.); U.S. Pat. No. 6,730,397 (Melancon et al.); U.S. Pat. No. 8,822,559 (Zoller et al.); and U.S. Pat. No. 8,822,560 (Seth et al.) and U.S. Patent Publication Nos. 2011-0206924 (Liu et al.), 2014-0220843 (Liu et al.), 2015-0165087 (Fung et al.), 2015-0376345 (Liu et al.), 2017/081573 (Kipke et al.), 2015/299542 (Determan et al.), 2013/040073 (Pett et al.), and 2015/259495 (Liu et al.), all of which are incorporated by reference in their entirety herein. In some embodiments, the adhesive also preferably has good release from a liner that will be used on the rear (or back or bottom) major surface of the backing.

In some embodiments, the adhesive is a pressure-sensitive adhesive (PSA). Some exemplary suitable classes of pressure-sensitive adhesives include polyacrylate adhesives, polyalphaolefin adhesives, polyvinyl acrylates, rubber resin adhesives, silicone adhesives, polydiorganosiloxane polyurea copolymers, mixtures or the like. Some exemplary suitable rubber resin adhesives include those formed using a tackified elastomer where a preferred elastomer is an A-B type block copolymer wherein the A blocks and B blocks are configured in linear (e.g. diblock or triblock copolymer), radial or star configurations. The A block can be formed of a mono-alkenylarene, preferably a polystyrene block having a molecular weight between 4000 and 50,000, preferably between 7000 and 30,000. The A block content is preferably about 10 to 50 weight percent, preferably about 10 to 30 weight percent of the block copolymer. Other exemplary suitable A blocks may be formed from alpha-methylstyrene, t-butyl-styrene and other ring alkylated styrenes, as well as mixtures thereof. The B block may be formed of an elastomeric conjugated diene, generally polyisoprene, polybutadiene or copolymers thereof having an average molecular weight from about 5000 to about 500,000, preferably from about 50,000 to about 200,000. The B block dienes can also be hydrogenated. In some embodiments, the B block content is generally 90 to 50 percent, preferably 90 to 70 percent by weight.

The pressure-sensitive adhesives or adhesive fibers can be mixed with particulates, such as sorbent particulate material, fumed silica, carbon black, glass beads, glass bubbles, clay particles, metal particles, and the like. Tackifiers (solid or liquid), plasticizers, colorants, end block resins, oils, cross-linkers, etc. may be included. Fillers, plasticizers, and other property modifiers, such as flow modifiers, dyes, pigments, flame retardants, stabilizers, antioxidants, compatibilizers, antimicrobial agents, electrical conductors, and thermal conductors, may be incorporated in the pressure-sensitive adhesive composition.

In some embodiments, the adhesive layer is applied to the entire rear (or back or bottom) major surface of the backing. In some embodiments, the adhesive does not cover the entire rear (or back or bottom) major surface of the backing. In some embodiments, the adhesive covers at least 50% of the backing, or at least 75%, or at least 90%, or at least 95% of the total surface of the rear (or back or bottom) major surface of the backing. In some embodiments, the adhesive is pattern coated onto the rear (or back or bottom) major surface of the backing. In some embodiments, the adhesive is coated on (for example, blowing on or roll coating), sprayed on, or laminated to the backing.

In some embodiments, the backing and adhesive form a conjugate multicomponent system, as described in, for example, U.S. Pat. No. 6,107,219 (Joseph et al.), incorporated by reference herein in its entirety. In such embodiments, the adhesive component layer or region and non-adhesive component layer or region are present in separate distinct regions in a conjugate multicomponent fiber. For example, multicomponent fiber layers or regions can be in the form of two, or more, overlaying layered fibers, sheath-core or concentric layered fiber arrangements or in "island in the sea" type fiber layer structures. One component region would comprise the adhesive component layer or region and a second component region would comprise the non-adhesive material layer or region. Generally the adhesive fiber component region will provide at least a portion of the exposed outer surface of the multicomponent conjugate fiber. Preferably, the individual components of the multi-component conjugate fibers will be present substantially continuously along the fiber length in discreet zones, which zones preferably extend along the entire length of the fibers.

In some embodiments, the backing and adhesive combination is breathable and/or porous. In some embodiments, the backing and adhesive combination is highly breathable and/or porous, making the support article comfortable to wear and/or to minimize or prevent itching, irritation, or undesirable skin reactions. In some embodiments, the backing and adhesive combination allows for moisture release. The more porous and/or breathable the backing and adhesive combination, the better the support article will release moisture caused by sweating or being worn in water or humid environments. In some embodiments, the backing and adhesive combination has a breathability and/or porosity of between about 6 and about 20 mm $H_2O$ measured using the pressure drop test. In some embodiments, the backing layer has a breathability and/or porosity of between about 10 and about 20 mm $H_2O$ measured using the pressure drop test. In some embodiments, the backing+adhesive combination has a breathability and/or porosity of at least about 6 mm $H_2O$ measured using the pressure drop test. In some embodiments, the backing+adhesive combination has a breathability of at least about 10 mm $H_2O$ measured using the pressure drop test. The breathability and/or porosity was measured using the pressure drop test described above.

In some embodiments, the backing and adhesive combination has a cross-directional tensile strength of between about 3 lbf (13.3 N) and about 11 lbf (48.9 N). In some embodiments, the backing and adhesive combination has a cross-directional tensile strength of between about 4 and about 10 lbf (44.5 N). In some embodiments, the backing and adhesive combination has a cross-directional tensile strength of greater than about 3 lbf (13.3 N). Tensile strength can be measured as described above.

In some embodiments, the backing and adhesive combination has a machine-directional tensile strength of between about 4 lbf (17.8 N) and about 15 lbf (66.7 N). In some embodiments, the backing and adhesive combination has a machine-directional tensile strength of between about 5 lbf (22.2 N) and about 13 lbf (57.8 N). In some embodiments, the backing and adhesive combination has a machine-directional tensile strength of greater than about 4 lbf (17.8 N). In some embodiments, the backing and adhesive combination has a machine-directional tensile strength of greater than about 6 lbf (26.7 N). In some embodiments, the backing and adhesive combination has a machine-directional tensile strength of less than about 15 lbf (66.7 N). In some embodiments, the backing and adhesive combination has a machine-directional tensile strength of less than about 12 lbf (53.4 N). Tensile strength can be measured as described above.

In some embodiments, the backing and adhesive combination has a cross-directional elongation at break of between about 600% and about 900%, or about 600% and about 800%. In some embodiments, the backing and adhesive combination has a cross-directional elongation at break of less than about 900% or less than about 800%. In some embodiments, the backing and adhesive combination has a cross-directional elongation at break of greater than about 600%. Elongation at break was measured as described herein.

In some embodiments, the backing and adhesive combination has a machine-directional elongation at break of between about 350% and about 1000%, or between about 450-550%. In some embodiments, the backing and adhesive combination has a machine-directional elongation at break of less than about 1000%, or about 900%, or about 800%, or about 700%, or about 600%. Elongation was measured as described herein. In some embodiments, the backing and adhesive combination has a machine-directional elongation at break of greater than about 350%, or about 4000%, or about 450%.

Adhesive Used to Adhere the Reinforcing Portion(s) or Strap(s) to the Backing:

Any of the adhesives described above or herein can be used to adhere the reinforcing portion(s), strap(s), or bump(s) to the backing or to each other. Where a different adhesive is used to adhere the reinforcing portion(s), strap(s), or bump(s) to the backing or to each other than the adhesive used to adhered the support article to the user, the adhesive can be any desired adhesive and need not be capable of use on skin since it would not necessarily be used directly on human skin. Additionally or alternatively, the adhesive need not have the porosity or breathability described above and/or herein. Additionally or alternatively, the adhesive need not have the same release properties from a liner described above and/or herein, since the adhesive may not be in contact with the liner. In some embodiments, the adhesive used to adhere the reinforcing portion(s), strap(s), or bump(s) to the backing or to each other may adhere more strongly than the adhesive used to adhere the support article to the user. Some exemplary suitable classes of pressure-sensitive adhesives that can be used to adhere the reinforcing portion(s), strap(s), or bump(s) to the backing or to each other include polyacrylate adhesives, polyalphaolefin adhesives, polyvinyl acrylates, rubber resin adhesives, silicone adhesives, polydiorganosiloxane polyurea copolymers, mixtures or the like.

Reinforcing Portion(s)

The reinforcing portion(s) can have a size, shape, thickness, material, etc. that allow the reinforcing portion(s) to be rigid enough to provide support, compression, and/or pain relief, conformable enough to permit ease of movement and comfort, and/or thin enough to provide a discreet material whose presence is not readily detectable under clothing. In some embodiments, it is preferred that the reinforcing portion not snap or break during use, which often happens with some existing braces that include plastic reinforcement materials. Any reinforcing portion that provides these qualities may be used. In some embodiments, the shape and/or size of the reinforcing portion is tailored for use on a specific area or region of the body. Exemplary reinforcing portion shapes include, but are not limited to, almond shapes, ellipses, ovals, circles, hemispheres, quadrilaterals, hexagons, heptagons, any shapes shown in the Figures of the present disclosure, etc. In some embodiments, the reinforcing portion(s) do not have adhesive on the user skin-facing major surface. In some embodiments, the reinforcing portion(s) have adhesive on the user skin-facing major surface. In some embodiments, where second reinforcing portions are present, they may include adhesive on both sides so that they can adhere to both the user and to the support article.

In some embodiments, the reinforcing portion is positioned between the backing and the user's skin, when the support article is in use. In some embodiments, the reinforcing portion is on the front (or top) major surface of the backing instead of being between the backing and the user's skin. For purposes of clarity, none of the figures show these embodiments, but any of the embodiments shown or described herein can include the reinforcing portion on the top (front) major surface of the backing.

In some embodiments, the reinforcing portion is a foam layer. In some embodiments, the reinforcing portion is a shaped memory foam layer. In some embodiments, the reinforcing portion is a shaped memory polymer such as, for example, those described in U.S. Patent Publication No. 2010/155998 (Rule et al.), the entirety of which is incorporated herein. In some embodiments, the foam layer includes at least one of polyethylene ("PE"), cross-linked PE, polyurethane, reticulated (open cell) foam, unreticulated (closed cell) foam, neoprene, melamine, vinyl nitrile, PET, XPS (extruded 1-polystyrene), EPS (expanded polystyrene), phenolic, EPP (expanded polypropylene), and EPE (expanded polyethylene). In some embodiments, the reinforcing portion includes a foam layer as described in U.S. Provisional Patent Application No. 62/429,401 (Young et al.), assigned to the present assignee, the entirety of which is incorporated herein.

In some embodiments, the reinforcing portion includes a multilayer construction. In some embodiments, the multilayer construction includes an adhesive layer between first and second foam layers and that construction between first and second skin layers. In other words, the outermost layer is a first skin layer adjacent to a first foam layer adjacent to an adhesive layer adjacent to a second foam layer adjacent to an outer second skin layer. In some embodiments, one or more of the foam layers include microspheres or expandable microspheres. In some embodiments, the microspheres are at least partially embedded in the adhesive layer. In some embodiments, at least one of the skin layers is substantially free of microspheres. In some embodiments, both skin layers are substantially free of microspheres. In some embodiments, the expandable microspheres in one or more of the foam layer are homogenously distributed throughout the foam layer. In some embodiments, the expandable microspheres in one or both of the foam layers are present in a range of between about 4 wt % to about 35 wt % or about 5 wt % to about 25 wt %, based on the total weight of the respective first and second pluralities of expandable microspheres.

Where present, the microspheres may be compressible and retain their spherical shape and integrity after compression, resulting in the reinforcing portion being very resilient and having a high restoration force. During use/wear of the support article, the reinforcing portion(s) readily conform to user movement but continue to provide support because the expanded spheres are resilient and provide strength and support before, during, and after compression. The force exerted to restore the support article is greater than a traditional open cell foam because the microspheres are compressed and have a higher restoration force vs. traditional foam. The microsphere foam is unique in that the more microspheres are added the higher the restoration force due to the increase in number of microspheres present. In a traditional open or closed cell foam a decrease in density typically results in a decreased restoration force because there is a reduction in the amount of polymer present. In the microsphere foam the shell of the microspheres provides a large part of the restoration force—in a traditional foam the polymer itself provides the restoration force—lower density traditional foam=less polymer=lower restoration force.

In some embodiments, the expandable microsphere loading is between about 3% and about 50%. In some embodiments, the microsphere loading is greater than about 3% or greater than about 5%, or greater than about 7%. In some embodiments, the microsphere loading is less than about 50% or less than about 45%, or less than about 40%, or less than about 35%, or less than about 25%, or less than about 15%, or less than about 10%. This resulted in a lightweight, conformable (compressible) foam structure with reduced density loading.

Figure 15:
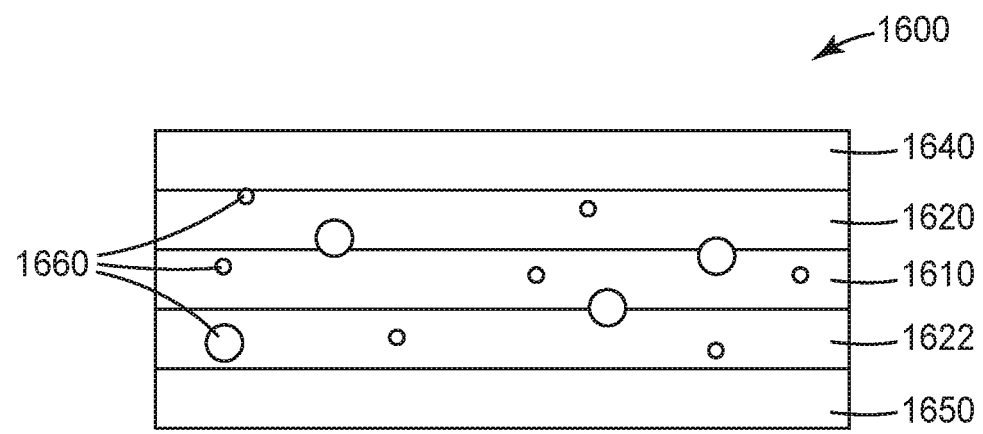
FIG. 15 is a cross-sectional schematic drawing of an exemplary reinforcing portion that can be used in the support articles of the present disclosure.

A schematic cross section of an exemplary construction as described above is shown in FIG. 15 in which reinforcing portion 1600 includes an adhesive layer 1610 whose first and second major surfaces 1612, 1614 are each adjacent to first and second foam layers 1620, 1622. First foam layer 1620 is adjacent to a first skin layer 1640, and second foam layer 1622 is adjacent to a second skin layer 1650. First and second skin layers 1640 and 1650 give reinforcing portion 1600 rigidity, while first and second foam layers 1620, 1622 provide softness, resiliency, and conformability. Microspheres 1660 are in at least some of the adhesive 1610 and first and second foam layers 1620, 1622. More information about each layer of these embodiments of the reinforcing portion is below.

Skin Layer(s):

Exemplary skin layers include, for example, at least one of a polyethylene, a polypropylene, a polyurethane, a polylactic acid, ethylene and methacrylate ester copolymer, or copolymers thereof. In some embodiments, at least one of the skin layers includes at least one of a polyolefinic material (e.g., polypropylene and/or polyethylene), modified polyolefinic material, polyvinyl chloride, polycarbonate, polystyrene, polyester (including co-polyester), polylactide, polyvinylidene fluoride, (meth)acrylic (e.g., polymethyl methacrylate), urethane, acrylic urethane, ethylene vinyl acetate copolymer, acrylate-modified ethylene vinyl acetate polymer, ethylene acrylic acid copolymers, nylon, engineering polymer (e.g., a polyketone and/or polymethylpentane), or elastomer (e.g., natural rubber; synthetic rubber; styrene block copolymer containing isoprene, butadiene, or ethylene (butylene) blocks; metallocene-catalyzed polyolefin, polyurethanes; or polydiorganosiloxane). First and second skin layers can be the same or different in composition, density, thickness, etc.

In some embodiments, the use of skins to increase stiffness is highly effective due to the fact that the stiffness of a material increases with the cube of the thickness. In some embodiments, strategically placing the skins on the outer portion of the foam layers provides high relative stiffness in a thin layer while retaining the compression and resilience provided by a foam. If the entire structure were foam without skins, the thickness of the total reinforcing portions could be significantly greater. In some embodiments, combining a resilient, compressible foam with non-foamed (or minimally foamed) skin layer(s) results in a thinner reinforcing portion than of comparable modulus vs. that of a monolithic foamed layer. In some embodiments, the skins also provide tear strength to the foamed layer.

Foam Layer(s):

Exemplary foam layers include, for example, at least one of a polyethylene, a polyurethane, a polylactic acid, a polypropylene, an ethylene and methacrylate ester copolymer, or copolymers thereof. First and second foam layers can be the same or different in composition, density, thickness, etc.

Adhesive Layer:

The adhesive can be any one of a number of pressure sensitive adhesives or non-pressure sensitive adhesive. Examples of suitable pressure sensitive adhesives include a natural rubber-based adhesive, a synthetic rubber based adhesive, a styrene block copolymer-based adhesive, a polyvinyl ether-based adhesive, a poly(methyl acrylate)-based adhesive, a polyolefin-based adhesive, or a silicone-based adhesive. As used herein, an adhesive that is "based" on a particular component means that the adhesive includes at least 50 wt. % of the particular component, based on the total weight of the adhesive. An exemplary adhesive is available under the designated trade designation "KRATON MD6748" from PolyOne Suitable non-pressure sensitive adhesives include those that "self-bond" or "block" at the temperature at which the polymeric multilayer material is extruded. Examples of suitable non-pressure sensitive adhesives include very low density polyethylene resins or ethylene copolymer resins with high comonomer content such as a high vinyl acetate containing ethylene vinyl acetate resin.

In some embodiments, the one or more reinforcing portions have a Shore A durometer hardness of between about 10 and about 100. In some embodiments, the one or more reinforcing portions have a Shore A durometer hardness of at least about 10, or at least about 20, or at least about 30, or at least about 40, or at least about 50. In some embodiments, the one or more reinforcing portions have a Shore A durometer hardness of less than about 100, or less than about 90, or less than about 80. In some embodiments, the one or more reinforcing portions have a Shore A durometer hardness of between about 50 and about 80. Shore A durometer hardness can be measured according to ASTM D2240 (2000) using testing equipment commercially obtained as "MODEL #8 SHORE A AND MODEL #9 SHORE D" from Pacific Transducer Corp (PTC Instruments), Los Angeles, Calif.

In some embodiments, the one or more reinforcing portions have a Shore D durometer hardness of between about 10 and about 60. In some embodiments, the one or more reinforcing portions have a Shore D durometer hardness of at least about 10, or at least about 20, or at least about 30. In some embodiments, the one or more reinforcing portions have a Shore D durometer hardness of less than about 60, or less than about 50. In some embodiments, the one or more reinforcing portions have a Shore D durometer hardness of between about 30 and about 50. Shore D durometer hardness can measured according to ASTM D2240 (2000) using testing equipment commercially obtained as "MODEL #8 SHORE A AND MODEL #9 SHORE D" from Pacific Transducer Corp (PTC Instruments), Los Angeles, Calif.

In some embodiments, the reinforcing portion(s) has a cross-directional tensile strength of between about 13 lbf (57.8 N) and about 28 lbf (129.0 N). In some embodiments, the reinforcing portion(s) has a cross-directional tensile strength of greater than about 13 lbf (57.8 N) or greater than about 15 lbf (66.7 N). In some embodiments, the reinforcing portion(s) has a cross-directional tensile strength of less than about 28 lbf (129.0 N) or less than about 25 lbf (111.2 N). Tensile strength is measured as described herein.

In some embodiments, the reinforcing portion(s) has a machine-directional tensile strength of between about 16 lbf (71.2 N) and about 31 lbf (137.9 N). In some embodiments, the reinforcing portion(s) has a machine-directional tensile strength of between about 18 lbf (80.1 N) and about 28 lbf (124.6 N). In some embodiments, the reinforcing portion(s) has a machine-directional tensile strength of greater than about 16 lbf (71.2 N), or greater than about 20 lbf (89.0 N). In some embodiments, the reinforcing portion(s) has a machine-directional tensile strength of less than about 31 lbf (137.9 N) or less than about 28 lbf (124.6 N). Tensile strength is measured as described herein.

In some embodiments, the reinforcing portion is relatively thin or low profile compared to a brace. In some embodiments, the reinforcing portion has a thickness of less than 2 cm (787 mil), or less than 1.5 cm (591 mil), or less than 1 cm (394 mil), or less than 0.5 cm (197 mil), or less than 0.25 cm (98 mil). In some embodiments, the reinforcing portion is 100 mil (0.254 cm), or less than 90 mil (0.229 cm), or less than 80 mil (0.203 cm), or less than 70 mil (0.178 cm), or less than 60 mil (0.152 cm), or less than 50 mil (0.127 cm), or less than 40 mil (0.102 cm), or less than 30 mil (0.076 cm), or less than 20 mil (0.051 cm). In some embodiments, the reinforcing portion has a thickness of at least 20 mil (0.051 cm), at least 30 mil (0.076 cm), or at least 50 mil (0.127 cm). In some embodiments, the reinforcing portion has a thickness of between about 0.025 cm (9.8 mil) to about 0.155 cm (61 mil).

In some embodiments, the reinforcing portion has a density of between about 0.20 g/cm$^3$ to about 0.60 g/cm$^3$, or in some embodiments, 0.25 g/cm$^3$ to 0.4 g/cm$^3$.

In some embodiments, the reinforcing portion(s) is generally non-elastic. In some embodiments, the reinforcing portion(s) have an elongation at break of between about 10% and about 50%, or between 15% and about 25%.

In some embodiments, the support article and/or reinforcing portion(s) has a compression of at least 40 mm Hg, or at least 41 mm Hg, or in some embodiments, 42 mm Hg.

In some embodiments, the reinforcing portion(s) are relatively non-absorbent. A reinforcing portion is considered relatively non-absorbent if, after submersion of a 10 gram sample of the reinforcing portion in water at room temperature for 24 hours followed by removing any visible traces of water from the exterior surface of the sample with a tissue, the mass of the sample increases by less than 20% by weight. In some embodiments the mass of such a sample may increase by less than 10% by weight, less 5% by weight, or even less than 1% by weight.

In some embodiments, the reinforcing portion covers at least 10% of the total surface area of the backing, or at least 15%, or at least 20%. In some embodiments, the reinforcing portion covers no greater than 75% of the total surface area of the backing, or no greater than 70%, or no greater than 60%.

Release Liner

Some embodiments of the present disclosure also include a release liner. Commercially available release liners that can be used include, for example, Polyslik®, PrimeLiner®, Film Plus®, or Lopasil® from Loparex, Cary, N.C.; and CF2 from The Griffin Network, Fallsington, Pa.

Strap:

In some embodiments, the strap can be made of any material that can stretch and/or extend by at least about 25%, or by at least about 50%. In some embodiments, the strap is made of the same material as the backing. In some embodiments, the strap is made of a different material than the backing. Some exemplary materials for the strap include, for example, polyolefinic material (e.g., polypropylene and/or polyethylene), modified polyolefinic material, polyvinyl chloride, polycarbonate, polystyrene, polyester (including co-polyester), polylactide, polyvinylidene fluoride, (meth)acrylic (e.g., polymethyl methacrylate), urethane, acrylic urethane, ethylene vinyl acetate copolymer, acrylate-modified ethylene vinyl acetate polymer, ethylene acrylic acid copolymers, nylon, engineering polymer (e.g., a polyketone and/or polymethylpentane), or elastomer (e.g., natural rubber; synthetic rubber; styrene block copolymer containing isoprene, butadiene, or ethylene (butylene) blocks; metallocene-catalyzed polyolefin, polyurethanes; or polydiorganosiloxane). In some embodiments, the strap provides customizable compression or pressure. Some commercially available strap materials include 3M MEDICAL TAPE 9907HTW and 3M TAN HI TACK NONWOVEN MEDICAL TAPE, both of which are made or sold by 3M Company of St. Paul, Minn.

In some embodiments, a portion of the strap is attached or adhered to a portion of the backing. In some embodiments where the strap is adhered, the adhesive is any adhesive that securely affixes the strap to the backing. Some exemplary adhesives include any of the adhesives described herein. Some additional exemplary adhesives include, for example, acrylate, natural rubber-based adhesive, a synthetic rubber based adhesive, a styrene block copolymer-based adhesive, a polyvinyl ether-based adhesive, a poly(methyl acrylate)-based adhesive, a polyolefin-based adhesive, or a silicone-based adhesive.

In some embodiments where a portion of the strap is mechanically attached or affixed to a portion of the backing, the strap can be attached by ultrasonic welding, extrusion, co-extrusion, RF welding, hook and loop, etc.

In some embodiments, the strap occupies between about 5% and about 80% of the total surface area of the front major surface of the backing, or between about 10% and about 60%, or between about 30% and about 50%. In some embodiments, the strap occupies at least about 5% of the total surface area of the front major surface of the backing, or at least about 10%, or at least about 20%, or at least about 30%. In some embodiments, the strap occupies less than 80% of the total surface area of the front major surface of the backing, or less than about 70%, or less than about 60%, or less than about 50%.

Bump

The bump can be any desired size, shape, thickness, etc that permits it to assist in providing targeted, localized contact and/or pressure to the affected area. Exemplary reinforcing shapes include, but are not limited to, almond shapes, ellipses, ovals, circles, hemispheres, quadrilaterals, hexagons, heptagons, top hat, cylindrical, flat top, concave top, convex top, square, rectangular, etc. The sides of the bump can be rounded or straight. Rounded side bumps will generally lack corners and thus may be desirable in some application. Those bumps with sides may include, for example, tapered sides. A variety of exemplary bump shapes and sizes are shown in FIGS. 8-13, each of which is a perspective schematic view of an exemplary bump for use with any of the support articles described herein. Some commercially available bumps are those sold as 3M Bumpon™ protective products, and of which can be used with the support articles described herein.

In some embodiments, the bump includes or is made of a polymer, a plastic, a layered nonwoven or woven, foam, gel pad, air pillow, metal, wood. In some embodiments, the bump(s) are polyurethane and their rear surface is coated with a pressure sensitive adhesive. Urethane can be a desired composition in some application because it is a durable, resilient elastomer. Further, urethane provides long aging resiliency (it will not crack or harden over time), good abrasion resistance, and resists marring or staining during use. In some embodiments, the pressure sensitive adhesive includes at least one of natural rubber, synthetic rubber, acrylic, or silicone. The bump can be colored or clear. Where the bump is colored, it may be, for example, skin colored, white, black, brown, gray, etc. In some embodiments, the bump is transparent. In some embodiments, the bump is colored and transparent.

In some embodiments, the bump has a height (or thickness projecting from the backing) of between about 1.0 mm and about 40.0 mm, more preferably between about 5.0 mm and about 20 mm, or between about 2 mm and about 10 mm. In some embodiments, the height is greater than 1.0 mm, or greater than 5.0 mm, or greater than 10.0 mm, or greater than 15.0 mm. In some embodiments, the bump has a height of less than about 40 mm, less than about 20 mm, less than about 15 mm, or less than about 10 mm. All dimensions are measured without an adhesive liner on the bump.

In some embodiments, the bump has a width of between about 2 mm and about 50 mm, or between about 5 mm and about 30 mm, or between about 8 mm and about 20 mm. In some embodiments, the bump has a width of greater than about 2 mm, or about 5 mm, or about 8 mm, or about 10 mm. In some embodiments, the bump has a width of less than about 50 mm, or 40 mm, or 30 mm, or 20 mm, or 15 mm. All dimensions are measured without an adhesive liner on the bump.

In some embodiments, the bump has a size that is between about 10% and about 80% of the total area of the backing. In some embodiments, the bump has a size that is between about 15% and about 50% of the total area of the backing.

In some embodiments, the bump has a Shore M hardness of between about 70 and 80, or about 72 and 75. Shore M hardness is measured according to ASTM D2240. In some embodiments, the bump has a resilience percent of between about 3% and about 35%, or between about 5% and about 30%. Resilience is measured according to ASTM-D2632 with a 0.125 inch sample. In some embodiments, the bump has a tensile strength of between about 550 and about 750 lbs/in$^2$ or between about 4 and 5.3 MPa$^2$. Tensile strength of the bump can be measured according to ASTM-D412, Die A. In some embodiments, the bump has excellent 90 degree peel adhesion. To obtain maximum surface adhesion, the surface to which the bump is applied is preferably at least one of unified, dry, and free of contaminants when the bump is applied. During application, the bump is preferably applied with some pressure and allowed time (dwell) to dry or set before use or further manufacturing.

Some embodiments have a single bump. Some embodiments have more than one bump. The bumps in embodiments having more than one bump can have different sizes, shapes, thicknesses, materials, etc.

Support Article:

In some embodiments, the support article is a patch, cove, sheet, or strip. In some embodiments, the support article is water resistant. In some embodiments, the support article can be worn for multiple days. In some embodiments, the support article can be worn for up to three (3) days. In some embodiments, the support article will not come off when exposed to humid environments or activities including, for example, in the shower, in humid environments, during exposure to sweat, and/or while swimming. In some embodiments, the support article is easy to apply and/or easy to remove. In some embodiments, the support article provides compression.

In some embodiments, the support article is at least some of lightweight and/or comfortable to wear. In some embodiments, the support article has a weight of between about 20 gsm and about 500 gsm. In some embodiments, the support article has a weight of between about 30 gsm and about 300 gsm).

In some embodiments, the support article is conformable. In some embodiments, the support articles have a conformability of less than 13 inches (33.0 cm). In some embodiments, the support articles have a conformability of greater than about 8 inches (20.2 cm).

In some embodiments, the support article is low profile. In some embodiments, the entire support article (including the backing, adhesive, and reinforcing portion(s)) has a thickness of between about 10 mil (0.025 cm) and about 500 mil (1.27 cm).

In some embodiments, the support article includes at least one of a hot/cold formulation and/or a pain-reducing medication (e.g., lidocaine) as part of the support article. In some embodiments, the support article further includes a medicament. In some embodiments, the medicament is one of pain-reducing agent and/or an agent that provides for heating or cooling relative to body temperature (or the sensation of heating or cooling relative to body temperature).

In some embodiments, the medicament, hot/cold formulation, and/or a pain-reducing medication is applied to the reinforcing portion and/or to the adhesive that holds the backing adjacent to the user's skin. In such embodiments, it may be desirable that the reinforcing portion has minimal porosity and/or breathability to ensure that the hot/cold formulation and/or a pain-reducing medication only contacts the affected area of the user.

In some embodiments, the support article (or a portion thereof, such as the reinforcing portion) includes only a single plane of symmetry in the major surface. In some embodiments, the support article (or a portion thereof, such as a reinforcing portion) has rounded perimeters without straight regions and/or corners.

The following examples describe some exemplary constructions of various embodiments of the support articles and methods of making the support articles described in the present application. The following examples describe some exemplary constructions and methods of constructing various embodiments within the scope of the present application. The following examples are intended to be illustrative, but are not intended to limit the scope of the present application.

EXAMPLES

All parts, percentages, ratios, etc. in the examples and the rest of the specification are by weight, unless noted otherwise. Solvents and other reagents used were obtained from Sigma-Aldrich Chemical Company; Milwaukee, Wis. unless otherwise noted. The following abbreviations are used: cm=centimeters; mm=millimeters; in=inch; m=meters; RPM=revolutions per minute; kg=kilograms; oz=ounces; lb=pounds; Pa=Pascals; min=minutes; hr=hours; gsm=grams per square meter (g/m$^2$); DW=downweb (or alternatively MD=machine direction); CW=crossweb; lbf=pound-force; and N=Newton. The terms "weight %", "% by weight", and "wt %" are used interchangeably.

Test Methods

Tensile and Elongation Test

Tensile testing and percent elongation tests were performed using a commercially available tensile tester (obtained under the trade designation "ZWICK" from Zwick USA, Kennesaw, Ga.). Tensile and percent elongation testing was performed in the downweb (machine) direction (DW) and in the crossweb (transverse) direction (CW) for all test specimens. Test specimens were cut to be 1 inch (2.54 cm) in width (or in the instance of certain commercially available tapes obtained in 1 inch widths, such tapes were used directly, with the 1 inch width as the crossweb direction). Except where noted, the gauge length was 2 inches (5.08 cm) for downweb testing and 1 inch (2.54 cm) for crossweb testing. A 200 N load cell was used. Depending on the value measured (e.g, downweb or crossweb tensile strength) clamps were attached to downweb ends or crossweb ends of the specimen as appropriate. Crosshead speed was 10 inches/min (25.4 cm/min). For both downweb and crossweb specimens, the maximum force achieved during the test (i.e., tensile strength at break), and the strain at the force maximum (i.e., percent elongation at break), was recorded. Test specimens were tested in triplicate in each of the two principal directions and the results averaged for each of the two principal directions.

Hardness Test

The Shore Durometer Hardness Test (ASTM D-2240 (2000)) was used to measure hardness of foamed specimens (i.e., reinforcing portions). Using testing equipment commercially obtained as "MODEL #8 SHORE A AND MODEL #9 SHORE D" from Pacific Transducer Corp (PTC Instruments), Los Angeles, Calif.

Both Shore A and Shore D hardness were measured. Each Shore tester (SHORE A and SHORE D) was calibrated. To calibrate each tester, a dial on a gauge of each tester was moved to a zero position. From there a probe of each tester was pressed to a surface of a known hardness. The SHORE A tester was considered calibrated if the gauge read 55 and the SHORE D tester considered calibrated if the gauge read 28.

For each specimen, a 1 inch (2.54 cm) square was cut, and the specimen placed on a hard benchtop surface. The specimens were flattened on the surface and a probe of the respective testers was positioned over the specimen. The probe of the instrument was pressed to the specimen, and the equipment provided a readout on the gauge. In each instance, five test specimens were tested and the readouts were averaged. According to section 9.3 within test method D-2240, durometer readings below 20 or above 90 are not considered reliable. By this criterion, some of the test specimens were "too soft."

Density Test

A pycnometer was used to measure the density of each foamed specimen (i.e., reinforcing portion). The buoyancy force was measured according to ASTM D3575-14 (2014) ("Suffix W—test method B), using a pycnometer (obtained under the trade designation "DELTA RANGE" (Model AG204) from Mettler-Toledo, LLC, Columbus, Ohio). The density was then calculated using Archimedes' principal. That is, specimens were cut from the foam film and first weighed dry ($m_{dry}$). The specimens were then placed underwater (de-ionized water) to measure the buoyant force ($m_{buoyant}$) on the pycnometer. Using the formula below, and knowing the density of water is 1 g/cm$^3$, the density of the foamed specimen was calculated.

$$\rho_{foam} = \rho_{water}\left(\frac{m_{dry}}{m_{dry} - m_{buoyant}}\right)$$

Test specimens were tested in triplicate and the results averaged.

Conformability Test

Conformability of foamed specimens (i.e., reinforcing portions) was evaluated as follows. Rectangular test strip specimens 1 inch (2.54 cm) in width and 13 inches (33.02 cm) in length were cut from the foamed material to be tested. The test strip specimens were cut so that the length of the rectangular shaped specimen was in the downweb direction. Where the cut test strip specimens displayed initial curvature, the specimens were flattened by either allowing them to relax on a hard, flat surface for 1 day or by hand manipulation (e.g., by running a finger down the length of the specimen putting slight pressure opposite the curve). The major face of the flattened specimen was then draped over a 26-inch (66.04 cm) circumference heat-capable cylindrical roll of a commercially available laminator (Orca III Laminator available from GBC Pro-Tech, De Forest, Wis.), such that the specimen extended 50% of the circumference of the heat-capable roll (i.e., orthogonal to the length of the roll). The specimen was held in place by taping the ends of the specimen to the heat-capable roll with masking tape. In instances where the roll was heated, the roll was allowed to stabilize at the desired temperature prior to applying the specimen on the roll, and after applying the specimen to the roll, the specimen was allowed to equilibrate on the roll for a predetermined dwell time (0.5 minutes, 1 minute, 5 minutes, or 10 minutes). After the predetermined dwell time, the tape was removed and the specimen was removed from the roll, taking special care not to deform the resultant U-shaped curved specimen. The curved specimen was placed on a hard benchtop surface at ambient temperature (~70° F.), with the bottom center of the U-shaped curve contacting the bench top and the specimen ends pointing upward toward the ceiling. The linear distance (in inches) between the two ends of the test specimen was measured using a ruler at various relaxation times, the relaxation time starting from when the specimen was removed from the roll. Higher conformability values indicate lower conformability (e.g., a conformability value of 13 inches after a short relaxation time for a 13-inch test specimen indicates that test specimen was relatively rigid, having relaxed back to original flat form in a short period of time). Reported conformability results are an average of three measurements.

Examples 1A, 1B, and 1C

An adhesive, a tackified polyacrylate-based non-woven BMF-PSA, was prepared substantially as described at column 18, lines 16-29 (Adhesive Sample 2) of U.S. Pat. No. 6,107,219, onto a conventional polycoated liner. The basis weight of the adhesive was about 60 gsm (about 1.5 mils (0.04 mm) in thickness). A non-woven backing was prepared substantially as described at column 19, lines 48-55 (Backing Samples 8-10) of U.S. Pat. No. 6,107,219, except that HL-2812 PT (an extrudable grade permanent pressure sensitive hot melt adhesive available from H.B. Fuller, Minneapolis, Minn.) was used rather than KRATON PSA, and the backing further contained 3 wt % of a tan pigment (comprised of pre-blended polyurethane (80%)/pigment (20%) available as Product No. FBPUR2103-85-AE TAN from Clariant, Minneapolis, Minn., as described at column 18 lines 55-63 of U.S. Pat. No. 6,107,219).

Three different non-woven backings were prepared at three different basis weights: Example 1A had a basis weight of about 100 gsm (about 11.75 mils (0.298 mm) in thickness); Example 1B had a basis weight of about 150 gsm (about 14.17 mils (0.360 mm) in thickness); and Example 1C had a basis weight of about 200 gsm (about 18.42 mils (0.468 mm) in thickness). Each of the non-woven backings were laminated to the adhesive using a laminator, substantially as described at column 22, lines 1-11 (Example 1) of U.S. Pat. No. 6,107,219. The resulting adhesive-coated backings had the following total basis weights (backing with adhesive, excluding the liner): Example 1A: about 160 gsm (about 13.25 mils (0.337 mm) in total thickness, excluding the liner); Example 1B: about 210 gsm (about 15.75 mils (0.400 mm) in total thickness, excluding the liner); and Example 1C: about 260 gsm (about 19.92 mils (0.506 mm) in total thickness, excluding the liner).

The tensile strength and elongation of the adhesive-coated backing (liner free) in each of the down web and cross web directions as measured according to the Tensile and Elongation Test and results are presented in Table 1 below. Table 1 further includes comparative tensile strength and elongation data for commercially available tapes and wraps.

TABLE 1

Down Web and Cross Web Tensile Strength and Elongation Percent for Various Examples and Comparative Examples.

|  |  | Tensile Strength (lbf) | Elongation (%) |
|---|---|---|---|
| Example 1A | DW (2-inch gauge length) | 5.39 (24.0 N) | 470.94 |
|  | CW (1-inch gauge length) | 4.26 (18.9 N) | 648.32 |
| Example 1B | DW (2-inch gauge length) | 8.30 (36.9 N) | 522.05 |
|  | CW (1-inch gauge length) | 6.24 (27.8 N) | 635.31 |
| Example 1C | DW (2-inch gauge length) | 10.57 (47.02 N) | 496.34 |
|  | CW (1-inch gauge length) | 9.53 (42.4 N) | 612.47 |
| Comparative Example A | DW (2-inch gauge length) | 24.63 (109.6 N) | 162.46 |
|  | CW (1-inch gauge length) | 36.07 (160.4 N) | 42.58 |
| Comparative Example B | DW (2-inch gauge length) | 11.87 (52.80 N) | 108.29 |
|  | CW (1-inch gauge length) | 27.61 (122.8 N) | 19.07 |
| Comparative Example C | DW (2-inch gauge length) | 17.93 (79.76 N) | 229.09 |
|  | CW (1-inch gauge length) | 35.92 (159.8 N) | 28.98 |
| Comparative Example D | DW (2-inch gauge length) | 14.76 (65.66 N) | 195.37 |
|  | CW (1-inch gauge length) | 7.81 (34.7 N) | 166.27 |
| Comparative Example E | DW (2-inch gauge length) | 20.58 (91.54 N) | 156.65 |
|  | CW (1-inch gauge length) | 32.07 (142.7 N) | 43.47 |
| Comparative Example F | DW (2-inch gauge length) | 37.66 (167.5 N) | 451.20 |
|  | CW (1-inch gauge length) | 45.35 (201.7 N) | 22.16 |

Comparative Example A: MUELLER KINESIOLOGY TAPE, BLACK 1-STRIP ROLL kinesiology tape from Mueller Sports Medicine (Prairie du Sac, WI).
Comparative Example B: KT TAPE ™ KINESIOLOGY THERAPEUTIC TAPE, ORIGINAL BLACK cotton kinesiology tape from KT Health, LLC (American Fork, Utah).
Comparative Example C: KT TAPE ™ KINESIOLOGY THERAPEUTIC TAPE, PRO PINK synthetic kinesiology tape from KT Health, LLC (American Fork, UT).
Comparative Example D: 3M ™ COBAN ™ self-adherent wrap available from 3M Company (St. Paul, MN).
Comparative Example E: ACE ™ KINESIOLOGY TAPE available from 3M Company (St. Paul, MN).
Comparative Example F: ACE ™ ELASTIC BANDAGE available from 3M Company (St. Paul, MN).

Example 2

The reinforcing portion (a blown film foam) was prepared as follows. A seven layer film was produced using a seven layer annular stack die (obtained under the trade designation "COEX 7-LAYER" (Type LF-400) from Labtech Engineering, Samutprakarn, Thailand). Airflow to the die was manually controlled to achieve a blow up ratio of about 2:1. The bubble was subsequently collapsed about ten feet above die and rolled up. The feed materials were supplied by 7 independent 20 mm diameter extruders, each with about a 30:1 length to diameter ratio. A first extruder was used to melt and extrude an extrudable pressure sensitive adhesive (obtained under the trade designation "KRATON MD6748" from Polyone, Avon Lake, Ohio) into an inside channel of the annular stack die. A screw speed of 30 revolutions per minute was used. The melt temperature was maintained at 180° C. A second, third, fourth, fifth and sixth extruder were used to feed, to the next five channels of the annular stack die, a blend of an ethylene methyl acrylate (EMA) copolymer (obtained under the trade designation "ELVALOY 1609" from Dupont, Wilmington, Del.) and a masterbatch pellet containing a 65% concentration of an expandable microsphere (obtained under the trade designation "EXPANCEL 950 MB 80" from Akzo Nobel, Amsterdam, Netherlands). The blend ratio was maintained at 92% of the ethylene methyl acrylate and 8% of the microsphere masterbatch. Extruder speeds were maintained at 60 revolutions per minute. A seventh extruder was used to feed a low density polyethylene (LDPE) resin (obtained under the trade designation "PETROTHENE NA217000" from Lyondell-Basell, Houston, Tex.) to the outside channel of the annular stack die. A melt temperature of 190° C. was maintained. The extruder speed for this resin was maintained at 70 revolutions per minute. Because the bubble was subsequently collapsed, and the innermost layer of the film was a pressure-sensitive adhesive, the finished film, after edge trimming of the collapsed bubble, was in effect a five layer film where the outermost (or "skin") layers were the LDPE, the center layer was the result of the joining of two layers of the pressure sensitive adhesive, and layers 2 and 4 were each the product of the merging, while in the melt, of five original layers of the EMA with expandable microspheres. The blown film foam produced was 55-60 mils (1.40-1.52 mm) thick and designated as Example 2.

The blown film foam was tested for tensile properties, hardness, and density, as described above. The results are provided in Table 2, below. Additionally, a 118 mil (3.00 mm) thick commercially available foam (obtained under the trade designation "WOODBRIDGE #SM25WH" from Woodbridge Polyurethane, Troy, Mich.), indicated as Comparative Example G in Table 2, was also tested.

TABLE 2

Tensile Properties, Hardness, and Density of Example 2 and Comparative Foam.

|  |  | Tensile Strength (lbf) | Elongation (%) | Shore A Hardness | Shore D Hardness | Density (g/cm³) |
|---|---|---|---|---|---|---|
| Example 2 |  |  |  | 70 | 38 | 0.41 |
|  | DW (2-in gauge length) | 21.6 (96 N) | 22 |  |  |  |
|  | CW (1-in gauge length) | 17.8 (79 N) | 16 |  |  |  |
| Comparative Example G |  |  |  | Too Soft | Too Soft | 0.04 |
|  | DW (2-in gauge length) | 3.4 (15 N) | 360 |  |  |  |
|  | CW (1-in gauge length) | 3.1 (14 N) | 475 |  |  |  |

The blown film foams from Example 2 and Comparative Example G were evaluated according to the Conformability Test, at ambient roll temperature (~70° F./~21° C.) and at 90° F. (32° C., simulating human skin temperature) roll temperature, as described above.

Comparative Example H was a flexible stabilizing bar, 7.94 inches (20.2 cm) in length and 0.5 inches (1.27 cm) in width obtained from a commercially available adhesive knee support strip under the trade designation KT FLEX REINFORCED ADHESIVE STRIPS from KT Health, LLC, American Fork, Utah. Comparative Example H was evaluated in a similar fashion as described in the Conformability Test, except that the flexible stabilizing bar was used directly in the test without further modification. Notably, the key component to providing conformability measurement data is the conformability of the reinforcing portion. The adhesive coated backing has a minimal impact on conformability measurement data. The results are provided in Table 3, below.

TABLE 3

Dwell Time, Relaxation Time, and Relaxation Length at Varying Temperatures.

| | Temperature (° F.) | Dwell Time (minutes) | Relaxation Time (minutes) | Relaxation Length (inches (cm)) |
|---|---|---|---|---|
| Example 2 | 90 | 0.5 | 0.5 | 12 (30.5) |
| | 90 | 10 | 0.5 | 11.5 (29.2) |
| | ~70 | 0.5 | 0.5 | 12.3 (31.2) |
| | ~70 | 10 | 0.5 | 12 (30.5) |
| Comparative Example G | 90 | 0.5 | 0.5 | 13 (33.0) |
| | 90 | 10 | 0.5 | 13 (33.0) |
| | ~70 | 0.5 | 0.5 | 13 (33.0) |
| | ~70 | 10 | 0.5 | 13 (33.0) |
| Comparative Example H | 90 | 0.5 | 0.5 | 7.94 (20.2) |
| | 90 | 10 | 0.5 | 7.94 (20.2) |
| | ~70 | 0.5 | 0.5 | 7.94 (20.2) |
| | ~70 | 10 | 0.5 | 7.94 (20.2) |

It is apparent from Table 3 that Comparative Examples G and H were largely non-conformable under the test conditions, with both relaxing to their original length after a relaxation time of only 30 seconds.

Example 3: Shoulder Support Article

A shoulder support article as shown in FIGS. 6 and 7B was made by laser cutting the adhesive-coated backing of the type described in Example 1B to the shape shown in FIG. 6. The reinforcing portion from Example 2 was laser cut to the shapes shown in FIG. 7B to form the reinforcing portions. The reinforcing portions were then laminated to the adhesive side of the adhesive coated backing. A conventional liner was then applied to the adhesive face of the article (covering both the adhesive layer of the backing as well as the reinforcing portion).

An adhesive elastic strap piece was made and applied to the front (or top) major surface of the adhesive-coated backing, opposite to the adhesive coated face of the backing, in the following manner. A commercially available elastic medical tape with an aggressive acrylate adhesive and further including a liner (available from 3M Company (St. Paul, Minn.) under the trade designation 9907HTW WHITE HI TACK NONWOVEN MEDICAL TAPE, "3M 9907HTW") was laser cut in the shape as shown in FIG. 7B. The liner of the strap was scored in the center of the strap (i.e., to cut the liner in half), orthogonally to the length of the strap, and the two portions of the liner adjacent to the score were folded backward to expose a generally square-shaped central adhesive region. The strap was then centered over non-adhesive face of the backing and adhered to the backing through the exposed central adhesive region using finger pressure, providing the shoulder support article. A similar shoulder support article could be prepared substituting the strap made from 3M 9907HTW with a strap made from a different commercially available elastic medical tape (3M TAN HI TACK NONWOVEN MEDICAL TAPE, "3M 9904").

The length of the resulting article in the longest direction was about 6.30 inches (16.0 cm). The length of the reinforcing portion in the longest direction was about 3.15 inches (8.00 cm). Approximately 85% of the surface area of the skin-facing side of the article was adhesive-coated (with the balance of the surface area occupied by the reinforcing portion). Other support articles described herein can be made in a similar fashion.

Example 4: Knee Support Article

A first knee support article as shown in FIGS. 2A and 2B was made by laser cutting an adhesive-coated backing of the shape shown in FIG. 2A from the backing/adhesive combination described in Example 1B. Two reinforcing portions of the shape and relative size shown in FIG. 2B were laser cut from the forma described in Example 2. The reinforcing portions were then laminated to the adhesive side of the adhesive coated backing. A conventional liner was then applied to the adhesive face of the article (covering both the adhesive layer of the backing as well as the reinforcing portions).

An adhesive elastic strap piece was made and applied to the front (or top) major surface of the adhesive-coated backing, opposite to the adhesive coated face of the backing, in the following manner. A commercially available elastic medical tape with an aggressive acrylate adhesive and further including a liner (available from 3M Company (St. Paul, Minn.) under the trade designation 9907HTW WHITE HI TACK NONWOVEN MEDICAL TAPE, "3M 9907HTW") was laser cut in the shape as shown in FIG. 2A, and was about 3.62 inches (9.19 cm) in length in the longest direction of the strap. Next, the liner of the strap was scored in the center of the strap (i.e., to cut the liner in half), orthogonally to the length of the strap, and the two portions of the liner adjacent to the score were folded backward to expose a square-shaped central adhesive region, measuring approximately 0.56 inches (1.4 cm) long on each side (with the folded portions of the liner providing tabs for easy removal of the liners during use of the article). The strap was then centered over non-adhesive face of the backing and adhered to the backing through the exposed central adhesive region using finger pressure, providing the knee support article shown in FIGS. 2A and 2B. The 3M 9907HTW had the following properties: a downweb (2-inch gauge length) tensile strength of 5.68 lbf (25.3 N); a crossweb (2-inch gauge length) tensile strength of 3.86 lbf (17.2 N); a downweb elongation of 591%; and a crossweb elongation of 543%.

The tensile strength of the 3M 9907HTW strap was measured according to the Tensile Test (except that a 2-inch gauge length was used for measurements in both downweb and crossweb directions). The strap had a downweb tensile strength of 5.68 lbf (25.3 N) and a crossweb tensile strength of 3.86 lbf (17.2 N). The elongation at break of the 3M 9907HTW strap was measured according to the Elongation Test (except that a 2-inch gauge length was used for measurements in both downweb and crossweb directions). The strap had a downweb elongation at break of 591% and a crossweb elongation at break of 543%.

The length of the support article in the longest direction was about 6.93 inches (17.6 cm). The length of the longest reinforcing portion in the longest direction was about 3.15 inches (8.00 cm). Other support articles described herein can be made in a similar fashion.

PICOPRESS Compression/Pressure Test Procedure

To test the ability of the support article to apply pressure, a commercially available portable digital pressure gauge was used (available from Microlab Elettronica S.a.s, Roncaglia di Ponte San Nicolò (PD), Italy under the trade designation MICROLAB PICOPRESS). The instrument utilizes circularly-shaped transducer (an air-inflatable plastic bladder that is 5 cm in diameter) made of a biocompatible material. The transducer is tethered to the digital gauge via tubing. The transducer is placed between a test specimen (e.g., a bandage or an adhesive support article) and a substrate (e.g., a limb or rigid cylinder). The instrument incorporates a micro pump which is manually activated by introducing a known volume of air (2 mL) into the transducer and the micro pump is equipped with a detection sensor. The pressure detected by the transducer is measured by the digital gauge and visualized by means of an alphanumeric display on the gauge and expressed in mmHg.

Compression/Pressure Test Procedure A (PICOPRESS)

A rigid 3-inch (7.62 cm) diameter cylinder was used as a substrate (the cylinder was approximately 10-12 inches (25-64 cm) in length). The circularly-shaped transducer was adhered midway along the length of the cylinder with double-sided tape, and arranged such that the tether connecting the transducer to the digital gauge was generally parallel to the long axis of the cylinder (the tether further being secured with single-sided adhesive tape). Application of the test specimen (rectangularly-shaped, 2 inches (5.08 cm)×4.5 inches (11.43 cm)) onto the cylinder, over the transducer, involved two laboratory personnel. When fully placed, the test specimen was arranged on the cylinder such that the long edge of the specimen (i.e., the 4.5 inch edge) was wrapped around a portion of the circumference of the cylinder (i.e., orthogonal to the cylinder axis), midway along the length of the cylinder, with the center of the transducer located between the center of the specimen and the cylinder. First, the liner of the specimen was removed to expose the adhesive. Second, one of the short edges (i.e., a 2-inch edge) of the specimen was adhered midway along the length of the cylinder, with the short edge of the specimen 1 inch (2.54 cm) away from the center of the transducer, such that when the specimen was fully placed (by wrapping the specimen partly about the circumference of the cylinder), the transducer would be centrally located underneath the test specimen. The second short edge of the specimen was adhered to a paddle of a commercially available digital force gauge (available under the trade designation CHATILLON DFS from Ametek, Largo, Fla.). Using two hands, Person 1 held the cylinder with the axis of the cylinder parallel to the floor, with one hand holding one end of the cylinder and the other hand holding the other end, such that the first short edge was on top (facing the ceiling rather than the floor) and visible to Person 1. Facing Person 1, Person 2 pulled on the digital force gauge so as to apply 1 lb (4.45 N) of force to the specimen (i.e., force was applied in a direction parallel to the floor, with non-adhered portion of the specimen also being parallel to the floor). While applying 1 lb of force, Person 1 rotated the cylinder toward themselves until the test specimen completely covered the transducer and the entire specimen was almost completely adhered to the cylinder with the exception of a portion of the second short edge of the specimen which was still adhered to the paddle. Person 1 then removed the second short edge portion from the paddle and adhered the remaining portion of the specimen onto the cylinder. The digital pressure gauge was then operated, injecting a fixed quantity a fixed volume of air (2 mL) into the transducer and measuring the pressure. Pressure readings were obtained in triplicate and averaged.

Compression/Pressure Test Procedure B (PICOPRESS)

The procedure used in Pressure Test Procedure B was substantially identical to that described for Pressure Test Procedure A, except that after removing the liner from the specimen, the center of the specimen was held in place over the center of the transducer while applying 1 lb of force first to one edge while adhering that first edge to the cylinder and then applying 1 lb of force to the second edge while adhering that second edge to the cylinder. In all cases, the specimens were arranged such that the longest linear direction of the specimen was wrapped about the circumference of the cylinder (analogously to Pressure Test Procedure A, for rectangular specimens), with the center of the transducer located under the center of the specimen, between the specimen and the cylinder. Results are presented in Table 5, below.

TABLE 5

Compression Results

|  | Pressure Test Procedure | Pressure (mmHg (kPa)) |
|---|---|---|
| Comparative Example B | A | 34.0 (4.53) |
| Comparative Example C | A | 32.0 (4.27) |
| Comparative Example I** | B | 26.70 (3.56) |
| Example 4 (without the reinforcing portions)* | B | 52.00 (6.93) |
| Example 4* | B | 58.70 (7.83) |

*The strap was engaged to provide additional pressure by removing the strap release liners, linearly stretching the end of each strap by 1" (2.54 cm), as measured from the strap ends, and adhering each of the stretched strap ends to the backing.
**Comparative Example I is KT FLEX REINFORCED ADHESIVE STRIPS from KT Health, LLC, American Fork, UT. (a commercially available adhesive knee support strip (10 inches × 2 inches (25 cm × 5 cm) including a flexible stabilizing bar within the adhesive support strip)

TEKSCAN Pressure Test Procedure

To test the ability of the knee support article of the present disclosure to apply pressure, a commercially available foot pressure testing system was used (available from Tekscan, Inc., South Boston, Mass. under the trade designation F-SCAN SYSTEM). The system is typically used to provide in-shoe pressure and force information and relies on a thin sensor foil placed inside the shoe (i.e., a foot-shaped sensor pad). The thin sensor foil includes 25 pressure sensors per square inch. The system was modified to allow for pressure testing of knee support articles described herein. Specifically, the foot-shaped sensor pad was taped to a rigid 3-inch (7.62 cm) diameter cylinder (the cylinder was approximately 10-12 inches (25-64 cm) in length) using double sided tape, such that the toe area of the sensor pad was at one end of the cylinder and the heel area of the sensor pad was at the other end of the cylinder.

After removing the liner of the support article, the center of the knee support article was placed over center of the sensor pad, with the specimen being wrapped in the long direction around a portion of the circumference of the cylinder (i.e., orthogonal to the cylinder axis), over the sensor pad, analogously to that described in Pressure Test Procedure B. The F-SCAN SYSTEM software calculated pressure readings across the entire surface of the article and pressure readings averaged. The knee support article of Example 4 was used, and pressure readings were obtained at various degrees of strap engagement. More specifically, the strap was engaged to provide additional pressure by removing the strap liners, linearly stretching the end of each strap in the indicated amount (0.5 inches, 1.0 inches, or 1.5 inches), as measured from the strap ends, and adhering each of the stretched strap ends to the backing. The same knee support "platform" was used (i.e., backing, adhesive, and reinforcing portion), however new straps were used at each variation of strap engagement (i.e., the old strap was removed and a new strap was adhered to the backing). Testing was performed twice, with triplicate readings in each test, and the results averaged.

TABLE 6

Knee Support Pressure Data.

| Strap Position | Pressure, mmHg (kPa) |
|---|---|
| Strap unengaged (extended by 0 inches) | 11.37 (1.516) |
| Strap extended by 0.5 inches (12.7 mm) (28% elongation) | 20.17 (2.689) |
| Strap extended by 1.0 inch (25.4 mm) (56% elongation) | 43.96 (5.861) |
| Strap extended by 1.5 inches (38.1 mm) (84% elongation) | 56.37 (7.515) |

Reference throughout this specification to "one embodiment," "some embodiments," "one or more embodiments" or "an embodiment," whether or not including the term "exemplary" preceding the term "embodiment," means that a particular feature, structure, material, or characteristic described in connection with the embodiment is included in at least one embodiment of the certain exemplary embodiments of the present disclosure. Thus, the appearances of the phrases such as "in one or more embodiments," "in certain embodiments," "in one embodiment" or "in an embodiment" in various places throughout this specification are not necessarily referring to the same embodiment of the certain exemplary embodiments of the present disclosure. Furthermore, the particular features, structures, materials, or characteristics described herein may be combined in any suitable manner in any of the embodiments described herein.

The recitation of all numerical ranges by endpoint is meant to include all numbers subsumed within the range (i.e., the range 1 to 10 includes, for example, 1, 1.5, 3.33, and 10). Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the disclosure, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

All references mentioned herein are hereby incorporated by reference in their entirety.

With reference to the Figures, like numerals are used to designate like components throughout the set of Figures.

Those having skill in the art will appreciate that many changes may be made to the details of the above-described embodiments and implementations without departing from the underlying principles thereof. Further, various modifications and alterations of the present invention will become apparent to those skilled in the art without departing from the spirit and scope of the invention. The scope of the present application should, therefore, be determined only by the following claims and equivalents thereof.

What is claimed is:

1. A support article, comprising:
    a backing having a front major surface and a rear major surface;
    an adhesive adjacent to least a portion of the rear major surface of the backing, the adhesive capable of adhering the support article to a user; wherein the backing and adhesive combination has a cross-directional tensile strength of between 4 lbf (17.8 N) and 9 lbf (40.0 N) and/or a machine-directional tensile strength of between 5 lbf (22.2 N) and 10 lbf (44.5 N); and
    a strap attached or adhered to the front major surface of the backing, the strap comprising a material that can stretch and/or extend by at least 25%.

2. The support article of claim 1, wherein the strap includes at least one of the following: a polyolefin, a modified polyolefin, a polyvinyl chloride, a polycarbonate, polystyrene, polyester, polylactide, polyvinylidene fluoride, (meth)acrylic, urethane, acrylic urethane, ethylene vinyl acetate copolymer, acrylate-modified ethylene vinyl acetate polymer, ethylene acrylic acid copolymers, nylon, engineering polymer, or elastomer.

3. The support article of claim 1, further including a release liner adjacent to at least a portion of the adhesive.

4. The support article of claim 1, wherein the backing includes at least one of a polyolefin, polyester, polyalkylene, polyamide, polystyrene, polyarylsulfone, polydiene, polyurethane, polyurethane film, polyethylene film, polypropylene film, PVC film, nonwoven material, and/or woven material.

5. The support article of claim 1, wherein the backing includes conjugate multicomponent melt spun fibers.

6. The support article of claim 1, wherein at least one of the backing or the backing and adhesive combination has a breathability and/ porosity of between 3 and 12 mm H₂O measured using the pressure drop test.

7. The support article of claim 1, wherein the backing has a weight of between 25 gsm to 300 gsm.

8. The support article of claim 1, wherein at least one of the backing or the backing and adhesive combination has a cross-directional elongation at break of between 600% and 900% and/or a machine-directional elongation at break of between 350% and 1000%.

9. The support article of claim 1, wherein the backing has a thickness of 0.01 cm to 1 cm.

10. The support article of claim 1, wherein the adhesive is a pressure sensitive adhesive and is selected from at least one of the following adhesive classes:

polyacrylate adhesives, polyalphaolefin adhesives, polyvinyl acrylates, rubber resin adhesives, silicone adhesives, polydiorganosiloxane polyurea compolymers, and mixtures thereof.

11. The support article of claim 1, wherein the backing and adhesive form a conjugate multicomponent system.

12. The support article of claim 1, further including one or more reinforcing portions adjacent to at least a portion of the rear major surface of the backing or the front major surface of the backing.

13. The support article of claim 12, wherein the one or more reinforcing portions comprise:
   an adhesive layer having first and second major surfaces;
   a first foam layer adjacent to first major surface of the adhesive layer;
   a second foam layer adjacent to second major surface of the adhesive layer;
   a first skin layer adjacent to first foam layer; and
   a second skin layer adjacent to second foam layer.

14. The support article of claim 12, comprising at least two reinforcing layers that are on layered on one another.

15. The support article of claim 12, wherein the support article has a weight of between 20 gsm and 500 gsm.

16. The support article of claim 12, wherein at least one of the reinforcing portions is separate from the support article and can be independently applied by the user before the full support article is applied.

17. The support article of claim 1, wherein the support article is applied to or sized for application to at least one of the IT band, hip, calf, shin, quads, hamstrings, groin, hip flexor, gluteus, outer knee, inner knee, Osgood shlatter, back of knee, front of knee, Achilles tendon, ankle, ball of foot, top of foot, heel, toe, finger, SI joint, low back, middle back, ribs, spine, abdominal, neck, shoulder, rotator cuff, AC joint, wrist, elbow, thumb, bicep, and/or tricep.

18. A method of applying a support article, comprising:
   removing a liner from a rear major surface of the support article to expose an adhesive;
   positioning the support article adjacent to a user's body in a desired location;
   applying the support article to the user such that the adhesive contacts the user's skin;
   putting pressure on the support article to cause the adhesive to adhere to the user's skin;
   removing one or more liners from a rear major surface of a strap on the support article;
   grasping one or more portions of the strap and elongating it; and
   applying and extending the strap to the user such that the strap adhered to the support article or user's skin; wherein the support article comprises: a backing having a front major surface and a rear major surface; an adhesive adjacent to least a portion of the rear major surface of the backing, the adhesive capable of adhering the support article to a user; and a strap attached or adhered to the front major surface of the backing, the strap comprising a material that can stretch and/or extend by at least 25%; wherein the backing and adhesive combination has a cross-directional tensile strength of between 4 lbf (17.8 N) and 9 lbf (40.0 N) and/or a machine-directional tensile strength of between 5 lbf (22.2 N) and 10 lbf (44.5 N).

* * * * *

UNITED STATES PATENT AND TRADEMARK OFFICE
CERTIFICATE OF CORRECTION

| | | |
|---|---|---|
| PATENT NO. | : 11,510,804 B2 | Page 1 of 1 |
| APPLICATION NO. | : 16/465793 | |
| DATED | : November 29, 2022 | |
| INVENTOR(S) | : Diane L Emslander et al. | |

It is certified that error appears in the above-identified patent and that said Letters Patent is hereby corrected as shown below:

In the Claims

<u>Column 37</u>
Line 1, In Claim 6, delete "and/ porosity" and insert -- and/or porosity --, therefor.
Line 17, In Claim 10, delete "compolymers" and insert -- copolymers --, therefor.

Signed and Sealed this
Ninth Day of April, 2024

Katherine Kelly Vidal
*Director of the United States Patent and Trademark Office*